United States Patent
Toyoda et al.

(10) Patent No.: US 11,136,344 B2
(45) Date of Patent: Oct. 5, 2021

(54) PURIFICATION AGENT FOR SUGAR CHAIN OR GLYCOPEPTIDE, AND USE THEREOF

(71) Applicant: SUMITOMO BAKELITE CO., LTD., Tokyo (JP)

(72) Inventors: Masaaki Toyoda, Tokyo (JP); Takayuki Matsumoto, Tokyo (JP); Midori Sakaguchi, Tokyo (JP); Takahiro Katayama, Tokyo (JP)

(73) Assignee: SUMITOMO BAKELITE CO., LTD., Tokyo (JP)

( * ) Notice: Subject to any disclaimer, the term of this patent is extended or adjusted under 35 U.S.C. 154(b) by 0 days.

(21) Appl. No.: 16/638,563

(22) PCT Filed: Oct. 31, 2018

(86) PCT No.: PCT/JP2018/040499
§ 371 (c)(1),
(2) Date: Feb. 12, 2020

(87) PCT Pub. No.: WO2019/088167
PCT Pub. Date: May 9, 2019

(65) Prior Publication Data
US 2020/0216484 A1  Jul. 9, 2020

(30) Foreign Application Priority Data

Oct. 31, 2017 (JP) .............................. JP2017-210150
Nov. 27, 2017 (JP) .............................. JP2017-227180

(51) Int. Cl.
| | |
|---|---|
| *C07H 1/06* | (2006.01) |
| *B01D 15/00* | (2006.01) |
| *B01D 15/32* | (2006.01) |
| *B01J 20/26* | (2006.01) |
| *G01N 30/88* | (2006.01) |

(52) U.S. Cl.
CPC .............. *C07H 1/06* (2013.01); *B01D 15/00* (2013.01); *B01D 15/327* (2013.01); *B01J 20/261* (2013.01); *G01N 30/88* (2013.01)

(58) Field of Classification Search
None
See application file for complete search history.

(56) References Cited

U.S. PATENT DOCUMENTS

| | | |
|---|---|---|
| 2006/0264620 A1 | 11/2006 | Lee et al. |
| 2007/0241054 A1 | 10/2007 | Miyazawa et al. |
| 2010/0210458 A1 | 8/2010 | Katsuhara et al. |
| 2010/0300971 A1 | 12/2010 | Jiang et al. |
| 2011/0100915 A1 | 5/2011 | Kanda et al. |
| 2015/0219641 A1 | 8/2015 | Matsumoto |

FOREIGN PATENT DOCUMENTS

| | | |
|---|---|---|
| JP | 59-169532 A | 9/1984 |
| JP | 2006-7203 A | 1/2006 |
| JP | 2006-201091 A | 8/2006 |
| JP | 2007093585 A | 4/2007 |
| JP | 2007-326920 A | 12/2007 |
| JP | 2010-71707 A | 4/2010 |
| JP | 2010190602 A | 9/2010 |
| JP | 2016-180716 A | 10/2016 |
| WO | 2005/024419 A1 | 3/2005 |

OTHER PUBLICATIONS

Wohlgemuth et al., "Enhanced glyco-profiling by specific glycopeptide enrichment and complementary monolithic nano-LC (ZIC-HILIC/RP18e)/ESI-MS analysis" J Sep Sci vol. 33 pp. 880-890 (Year: 2010).*
Jiang et al., "Interactions in Capillary Electrophosesis Capillaries by Photografted Zwitterionic Polymer Surface Layers" Analytical Chemistry vol. 75 pp. 2768-2774 (Year: 2003).*
Jiang et al., "Novel zwitterionic polyphosphorylcholine monolithic column for hydrophilic interaction chromatography" Journal of Chromatography A vol. 1216 pp. 2439-2448 (Year: 2009).*
Yu et al., "Synthesis and evaluation of sulfobetaine zwitterionic polymer bonded stationary phase" Talanta vol. 161 pp. 860-866 (Year: 2016).*
Verzele et al., "Quality Criteria and Structure of Silica Gel Column Packing Material" Journal of Chromatography vol. 329 pp. 351-357 (Year: 1985).*
"Silica Gel 60 (230-400 Mesh) 25 Kg Silicar" publ;ished by Thomas Scientific, downloaded from www. thomassci.com (Year: 2020).*
Ma et al., "Electrospun regenerated cellulose nanofiber affinity membrane functionalized with protein A/G for IgG purification" Journal of Membrane Science vol. 319 pp. 23-28 (Year: 2008).*
Hernandez et al., "Development of a new method using HILIC-tandem mass spectrometry for the characterization of O-sialoglycopeptides from proteolytically digested caseinomacropeptide" Proteomics vol. 10 pp. 3699-3711 (Year: 2010).*
Chen et al.; "Interaction modes and approaches to glycopeptide and glycoprotein enrichment", Analyst, 2014, vol. 139, p. 688-704 (Total 18 pages), cited in Specification.
Tajiri et al.; "Differential analysis of site-specific glycans on plasma and cellular fibronectins: Application of a hydrophilic affinity method for glycopeptide enrichment", Glycobiology, 2005, vol. 15, No. 12, p. 1332-1340, (9 pages), cited in Specification.
Das et al.; "Induction of glycosylation in human C-reactive protein under different pathological conditions", Biochem. J., 2003, vol. 373, pp. 345-355, (11 pages), cited in ISR and Written Opinion.

(Continued)

*Primary Examiner* — Eric Olson
(74) *Attorney, Agent, or Firm* — Westermina, Hattori, Daniels and Adrian, LLP

(57) ABSTRACT

A purification agent which includes a compound having a betaine structure, and which is for a sugar chain having a length equal to or longer than that of a monosaccharide or for a glycopeptide having a sugar chain having a length equal to or longer than that of a monosaccharide.

12 Claims, 6 Drawing Sheets

(56) References Cited

OTHER PUBLICATIONS

International Search Report dated Feb. 5, 2019, issued in counterpart International Application No. PCT/JP2018/040499 (2 pages).

Written Opinion of the International Searching Authority dated Feb. 5, 2019, issued in counterpart International Application No. PCT/JP2018/040499 with English Translation (7 pages).

Written Opinion of the International Searching Authority dated Feb. 5, 2019, issued in counterpart International Application No. PCT/JP2018/040499 (7 pages).

Doco et al., "Complex Carbohydrates of Red Wine: Characterization of the Extreme Diversity of Neutral Oligosaccharides by ESI-MS", Journal of Agricultural and Food Chemistry, vol. 63, No. 2, Jan. 7, 2015, pp. 671-682 (in English; cited in Supplementary European Search Report dated Jul. 17, 2020, issued in counterpart European Patent Application No. 18872893.5).

Hetrick et al., "Evaluation of a hydrophilic interaction liquid chromatography design space for sugars and sugar alcohols", Journal of Chromatography A, vol. 1489, Jan. 27, 2017, pp. 65-74 (in English; cited in Supplementary European Search Report dated Jul. 17, 2020, issued in counterpart European Patent Application No. 18872893.5).

Palma, et al., "Evaluation of the Deuterium Isotope Effect in Zwitterionic Hydrophilic Interaction Liquid Chromatography Separations for Implementation in a Quantitative Proteomic Approach", Analytical Chemistry, vol. 83, pp. 8352-8356 (2011) (in English; cited in Opposition submitted in Japanese Patent No. 6669314 (Patent Application No. 2019-537017) on Oct. 23, 2020).

Seikagaku, The Japanese Biochemical Society, Japan, vol. 82, No. 6, p. 551 (Jun. 25, 2010) (w/ English machine translation; cited in Opposition submitted in Japanese Patent No. 6669314 (Patent Application No. 2019-537017) on Oct. 23, 2020).

Jiang et al., "Zwitterionic stationary phase with covalently bonded phosphorylcholine type polymer grafts and its applicability to separation of peptides in the hydrophilic interaction liquid chromatography mode", Journal of Chromatography A, vol. 1127, pp. 82-91 (2006) (in English; cited in Opposition submitted in Japanese Patent No. 6669314 (Patent Application No. 2019-537017) on Oct. 23, 2020).

Cajka, et al., "Toward merging untargeted and targeted methods in mass spectrometry-based metabolomics and lipidomics", Analytical Chemistry, vol. 88, pp. 524-545 (2016) (in English; cited in Office Action dated Dec. 2, 2020 in Japanese Patent Application No. 2019-537017).

Nettleship, J.E. "Chapter 3: Structural Biology of Glycoproteins", Glycosylation, edited by Stefana Petrescu, pp. 41-62, Sep. 26, 2012, IntechOpen, DOI: 10.5772/48154 (retrieved on Mar. 18, 2021, from https://www.intechopen.com/books/glycosylation/structural-biology-of-glycoproteins) (24 pages; in English; cited in Written Opinion issued in counterpart Japanese Application No. 2019-537017 (Japanese Patent No. 6669314) on Apr. 14, 2021)).

Naruken, "Column of glycans No. 5—What is O-glycans", Web page <https://soyaku.co.jp/column/1044/>, Homepage of Medicinal Chemistry Pharmaceutical, Co., Ltd., Aug. 31, 2016 (retrieved on Apr. 2, 2021, from https://soyaku.co.jp/column/1044/) (3 pages; w/ English machine translation; cited in Japanese Notice of Reasons for Revocation).

Notice of Reasons for Revocation dated Apr. 14, 2021, issued in counterpart Japanese Application No. 2019-537017 (Japanese Patent No. 6669314) (19 pages; English machine translation only).

\* cited by examiner

PURIFICATION AGENT FOR SUGAR CHAIN OR GLYCOPEPTIDE, AND USE THEREOF

TECHNICAL FIELD

The present invention relates to a carrier for purification and use thereof. More specifically, the present invention relates to a purification agent for a sugar chain having a length equal to or longer than that of a monosaccharide or a glycopeptide having a sugar chain having a length equal to or longer than that of a monosaccharide, a carrier for purification for a sugar chain having a length equal to or longer than that of a monosaccharide or a glycopeptide having a sugar chain having a length equal to or longer than that of a monosaccharide, a method for purifying a sugar chain having a length equal to or longer than that of a monosaccharide or a glycopeptide having a sugar chain having a length equal to or longer than that of a monosaccharide, a kit for purification of a sugar chain having a length equal to or longer than that of a monosaccharide or a glycopeptide having a sugar chain having a length equal to or longer than that of a monosaccharide, and an apparatus for purification of a sugar chain having a length equal to or longer than that of a monosaccharide or a glycopeptide having a sugar chain having a length equal to or longer than that of a monosaccharide.

Priority is claimed on Japanese Patent Application No. 2017-210150, filed on Oct. 31, 2017, and Japanese Patent Application No. 2017-227180, filed on Nov. 27, 2017, the contents of which are incorporated herein by reference.

BACKGROUND ART

Most of the proteins that make up the living body are glycosylated and present as glycoproteins to which a sugar chain is bonded. By such glycosylation, functions such as formation of higher order structure, and intercellular signaling and molecular recognition; in vivo kinetics; and the like of proteins are regulated. It is known that a structure and distribution of a sugar chain of this glycoprotein are involved in the functional expression of proteins, and a sugar chain structure changes in accordance with the onset and progression of many diseases. It is expected that structural analysis of glycoproteins plays an important role in elucidation of the onset mechanism of various diseases accompanied by sugar chain structural change, development of disease treatment and diagnostic technology, and the like, in various technical fields such as life sciences, medicine, and drug discovery.

Structural analysis of glycoproteins is generally carried out by analyzing glycopeptides and sugar chains obtained by degrading glycoproteins by enzyme digestion or the like. However, analysis is difficult because of a very small abundance of glycopeptides and sugar chains in the degradation product of glycoproteins, and the presence of a significantly large amount of peptides. Accordingly, there is a strong demand for the construction of a technique that can remove peptides to which a sugar chain is not bonded and can specifically concentrate only glycopeptides and sugar chains to which the sugar chain is bonded.

In the related art, various techniques have been reported as techniques for concentrating glycopeptides and the like. For example, a concentration technique using hydrophilic interaction; a concentration technique by covalent bond formation using phenylboronic acid and the like; a concentration technique using interaction with lectin; a concentration technique using chelate interaction with titanium (for example, titanium oxide ($TiO_2$)), zirconium, silver, or the like; and the like have been reported (refer to, for example, NPL 1 and the like). Herein, the concentration technique using hydrophilic interaction utilizes physicochemical properties of glycopeptides and the like, utilizes a hydrogen bond formed between a sugar chain and a hydroxyl group of sepharose, and thereby selectively capture and recover glycopeptides and the like by sepharose beads (refer to, for example, NPL 1, NPL 2, and the like). Specifically, a mixture of trypsin and lysyl endopeptidase, or a digested material obtained by enzymatic digestion of glycoproteins with chymotrypsin and the like is mixed with sepharose beads with an organic solvent (1-butanol/ethanol/water) (5:1:1, v/v) and the like, glycopeptides and the like are adsorbed to the sepharose beads and washed with the above organic solvent, and elution is performed with an aqueous solvent (ethanol/water) (1:1, v/v) and the like.

CITATION LIST

Non-Patent Literature

[NPL 1] Chen-Chun Chen et al., "Interaction modes and approaches to glycopeptide and glycoprotein enrichment", Analyst, 2014, vol. 139, p. 688-704

[NPL 2] Michiko Tagiri et al., "Differential analysis of site-specific glycans on plasma and cellular fibronectins: Application of a hydrophilic affinity method for glycopeptide enrichment", Glycobiology, 2005, vol. 15, no. 12, p. 1332-1340

SUMMARY OF INVENTION

Technical Problem

However, because interaction between sepharose and a sugar chain is weak in the concentration technique using sepharose beads reported in NPL 1, NPL 2, and the like, a glycopeptide having an O-glucoside-bonded sugar chain with a small molecular weight and a glycopeptide having a long peptide region are affected by peptides, and thereby holding with respect to sepharose beads is weakened. Accordingly, there is a problem of a deterioration in concentration efficiency and reproducibility of glycopeptides and the like.

Herein, when concentrating and purifying biomolecules, a batch method and a column method such as a spin column method are widely used. The batch method is a method in which a sample and a carrier are input to the same container and stirred for a certain period of time, and after adsorbing a target substance to the carrier, a liquid phase portion is removed using centrifugal force, magnetism, or the like, and thereby the target substance is concentrated. In a case where sepharose beads are applied as a carrier to the batch method, the sepharose beads do not form a clear solid-liquid separation surface because they absorb water and swell. For this reason, a liquid phase portion containing free peptide fragments and the like cannot be effectively removed. Furthermore, there is a risk of sample loss in which sepharose beads to which glycopeptides and the like are adsorbed are removed together with the liquid phase portion. This causes a deterioration in concentration efficiency and reproducibility of glycopeptides and the like.

The spin column method is a method in which a sample is input to a filter cup or the like filled with a carrier, a liquid in the sample is allowed to pass through by the carrier by using gravity, centrifugal force, and the like so that a target substance is adsorbed, a drained fluid after allowing the liquid to pass through is removed, and thereby the target substance is concentrated. However, a surface of sepharose beads becomes in a dry state while application of the sepharose beads as a carrier to the spin column method can easily realize solid-liquid separation by using a filter cup or the like. Sepharose beads are susceptible to drying and this may cause a decrease in a recovery percentage of glycopeptides, and therefore they are required to be handled carefully.

An object of the present invention is to provide a technique capable of specifically and efficiently capturing hydrophilic glycopeptides and sugar chains. Another object of the present invention is to provide a technique capable of efficiently concentrating glycopeptides and sugar chains at a high concentration level with a high purity level by a simple operation from samples contaminated with free peptide fragments and the like.

Solution to Problem

The inventors of the present invention have conducted intensive studies to achieve the above objects, and as a result, they have found that, by immobilizing a polymer in which a side chain having a betaine structure is bonded to a main chain on an insoluble support, it is possible to effectively improve hydrophilicity of the carrier. In addition, they have found that, the carrier has a characteristic capable of strongly holding a glycopeptide and a sugar chain with high hydrophilicity by hydrophilic interaction, and by utilizing such a characteristic, it is possible to efficiently concentrate glycopeptides and sugar chains at a high concentration level with a high purity level by a simple operation.

In other words, the present invention provides a carrier, a method for concentrating glycopeptides using the carrier, a method for concentrating sugar chains, a kit for concentration of glycopeptides, a kit for concentration of sugar chains, an apparatus for concentration of glycopeptides, and an apparatus for concentration of sugar chains. The present invention specifically includes the following configuration.

[1] A purification agent which includes a compound having a betaine structure, and which is for a sugar chain having a length equal to or longer than that of a monosaccharide or for a glycopeptide having a sugar chain having a length equal to or longer than that of a monosaccharide.

[2] The purification agent according to [1], in which the betaine structure is a structure represented by Formula (1).

$$Z-L-A \quad (1)$$

(In Formula (1), Z represents a cationic group selected from the group consisting of a secondary amino group, a tertiary amino group, a quaternary ammonium group, and an imino group; L represents an alkylene group having 1 to 10 carbon atoms; and A represents an anionic group selected from the group consisting of a phosphoric acid group, a carboxyl group, a phosphonic acid group, a phosphinic acid group, a sulfonic acid group, a sulfin group, a sulfene group, a hydroxyl group, a thiol group, and a boronic acid group.)

[3] The purification agent according to [1] or [2], in which the cationic group is a quaternary ammonium group.

[4] The purification agent according to any one of [1] to [3], in which the anionic group is a phosphoric acid group.

[5] The purification agent according to any one of [1] to [4], in which the betaine structure is a phosphorylcholine group.

[6] The purification agent according to any one of [1] to [5], in which the compound is a polymer in which a side chain having a betaine structure is bonded to a main chain.

[7] The purification agent according to [6], in which the polymer is a polymer of a monomer containing a (meth) acrylic compound.

[8] A carrier for purification of a sugar chain having a length equal to or longer than that of a monosaccharide or a glycopeptide having a sugar chain having a length equal to or longer than that of a monosaccharide, wherein the purification agent according to any one of [1] to [5] is immobilized on an insoluble support.

[9] A carrier for purification of a sugar chain having a length equal to or longer than that of a monosaccharide or a glycopeptide having a sugar chain having a length equal to or longer than that of a monosaccharide, wherein the purification agent according to [6] or [7] is immobilized on an insoluble support.

[10] The carrier for purification according to [9], in which a weight of the polymer immobilized on the insoluble support is 0.5 mg to 1.5 mg per unit surface area ($m^2$) of the insoluble support.

[11] The carrier for purification according to any one of [8] to [10], in which the insoluble support is formed of an inorganic substance.

[12] The carrier for purification according to any one of [8] to [11], in which a specific gravity is 1.05 to 3.00.

[13] The carrier for purification according to any one of [8] to [12], which is a spherical shape and has an average particle diameter of 0.5 µm to 100 µm.

[14] A method for purifying a sugar chain having a length equal to or longer than that of a monosaccharide or a glycopeptide having a sugar chain having a length equal to or longer than that of a monosaccharide, the method including: brining the purification agent according to any one of [1] to [7] or the carrier for purification according to any one of [8] to [13] into contact with a sample containing a sugar chain having a length equal to or longer than that of a monosaccharide or a glycopeptide having a sugar chain having a length equal to or longer than that of a monosaccharide and containing an organic solvent such that the sugar chain or the glycopeptide is adsorbed onto the purification agent or the carrier for purification; and bringing the purification agent or the carrier for purification into contact with water to elute the sugar chain having a length equal to or longer than that of a monosaccharide or the glycopeptide having a sugar chain having a length equal to or longer than that of a monosaccharide.

[15] A kit for purification of a sugar chain having a length equal to or longer than that of a monosaccharide or a glycopeptide having a sugar chain having a length equal to or longer than that of a monosaccharide, the kit including: the purification agent according to any one of [1] to [7] or the carrier for purification according to any one of [8] to [13]; and protocol information for using the kit.

[16] An apparatus for purification of a sugar chain having a length equal to or longer than that of a monosaccharide or a glycopeptide having a sugar chain having a length equal to or longer than that of a monosaccharide, the apparatus including: a container holding part that holds a container containing the purification agent according to any one of [1] to [7] or the carrier for purification according to any one of [8] to [13]; and a reagent introduction part that introduces a reagent into the container.

[P1] A carrier in which a polymer in which a side chain having a betaine structure is bonded to a main chain is immobilized on an insoluble support.

According to the above configuration, by immobilizing a polymer in which a side chain having a betaine structure is bonded to a main chain on an insoluble support, it is possible to provide a carrier of which hydrophilicity is effectively improved. The carrier has a characteristic capable of strongly holding a glycopeptide and a sugar chain with high hydrophilicity by hydrophilic interaction. In addition, the carrier can capture a glycopeptide having an O-glycosidic bond-type sugar chain and a glycopeptide having a long peptide region without being affected by a peptide. Accordingly, regarding the carrier, it is possible to provide a carrier that can efficiently concentrate glycopeptides and sugar chains at a high concentration level with a high purity level by a simple operation by utilizing such a characteristic, and that has a carrier having excellent operability and functionality.

[P2] The carrier of [P1] above, in which a cationic moiety of the betaine structure contains a quaternary ammonium group.

[P3] The carrier of [P1] or [P2] above, in which an anionic moiety of the betaine structure contains a phosphoric acid group.

[P4] The carrier of any one of [P1] to [P3] above, in which the betaine structure is phosphorylcholine.

[P5] The carrier of any one of [P1] to [P4] above, in which the polymer is composed of a polymer derived from monomers containing a (meth)acrylic compound.

According to the above configuration, it is possible to provide a carrier using a polymer that has significantly high hydrophilicity and biocompatibility and that is easily obtained and synthesized; and it is possible to provide a carrier that can further efficiently concentrate glycopeptides and sugar chains at a high concentration level with a high purity level.

[P6] The carrier of any one of [P1] to [P5] above, in which a weight of the polymer bonded to the insoluble support is 0.5 mg to 1.5 mg per unit surface area ($m^2$) of the insoluble support.

[P7] The carrier of any one of [P1] to [P6] above, in which the insoluble support is composed of an inorganic substance.

[P8] The carrier of any one of [P1] to [P7] above, which has a specific gravity of 1.05 to 3.00.

[P9] The carrier of any one of [P1] to [P8] above, which is a spherical shape and has an average particle diameter of 0.5 μm to 100 μm.

According to the above configuration, it is possible to provide a carrier having favorable sedimentation property, dispersibility, and the like and having further excellent operability. In addition, in a case of application for concentration of glycopeptides and sugar chains, and the like, it is possible to provide a carrier that is further excellent in terms of capture efficiency of glycopeptides and sugar chains and separation efficiency with free peptide fragments and the like.

[P10] The carrier of any one of [P1] to [P9] above, which is for concentration of glycopeptides.

According to the above configuration, it is possible to provide a carrier for concentration of glycopeptides, and the carrier has the characteristic capable of strongly holding a glycopeptide with high hydrophilicity by hydrophilic interaction, and thereby it is possible to efficiently concentrate a glycopeptide at a high concentration level with a high purity level by a simple operation.

[P11] The carrier of any one of [P1] to [P9] above, which is for concentrating a sugar chain.

According to the above configuration, it is possible to provide a carrier for concentration of sugar chains, and the carrier has the characteristic capable of strongly holding a sugar chain with high hydrophilicity by hydrophilic interaction, and thereby it is possible to efficiently concentrate a sugar chain at a high concentration level with a high purity level by a simple operation.

[P12] A method for concentrating a glycopeptide, which includes a step of concentrating a glycopeptide using the carrier described in any one of [P1] to [P10] above.

[P13] The method for concentrating a glycopeptide described in [P12] above, in which the step of concentrating a glycopeptide is a concentration step by a batch method or a spin column method.

According to the above configuration, it is possible to provide a method for concentrating a glycopeptide using the carrier of the present invention, and thereby it is possible to efficiently concentrate a glycopeptide at a high concentration level with a high purity level by a simple operation. In addition, the above configuration can be suitably applied to a batch method, a spin column method, and the like, and it is possible to efficiently concentrate a glycopeptide at a high concentration level with a high purity level by a simpler operation.

[P14] A method for concentrating a sugar chain, which includes a step of concentrating a sugar chain using the carrier described in any one of [P1] to [P9] and [P11] above.

[P15] The method for concentrating a sugar chain described in [P14] above, in which the step of concentrating a sugar chain is a concentration step by a batch method or a spin column method.

According to the above configuration, it is possible to provide a method for concentrating a sugar chain using the carrier of the present invention, and thereby it is possible to efficiently concentrate a sugar chain at a high concentration level with a high purity level by a simple operation. In addition, the above configuration can be suitably applied to a batch method, a spin column method, and the like, and it is possible to efficiently concentrate a sugar chain at a high concentration level with a high purity level by a simpler operation.

[P16] A kit for concentration of glycopeptides, which includes the carrier of any one of [P1] to [P10] above; and protocol information for using the kit.

According to the above configuration, it is possible to perform concentration of glycopeptides more simply by kitting a carrier and information necessary for concentration of glycopeptides.

[P17] A kit for concentration of sugar chains, which includes the carrier of any of [P1] to [P9] and [P11] above; and protocol information for using the kit.

According to the above configuration, it is possible to perform concentration of sugar chains more simply by kitting a carrier and information necessary for concentration of sugar chains.

[P18] An apparatus for concentration of glycopeptides, which includes a container holding part that holds a container capable of containing a sample that contains a glycopeptide, and into which the carrier of any one of [P1] to [P10] above is introduced; and a reagent introduction part that introduces reagents into the container.

[P19] The apparatus for concentration of glycopeptides of [P18] above, which further includes a solid-liquid separation part that is for solid-liquid separation of contents of the container.

According to the above configuration, it is possible to perform concentration of glycopeptides more simply by assembling a carrier and members necessary for concentration of glycopeptides.

[P20] An apparatus for concentration of sugar chains, which includes a container holding part that holds a container capable of containing a sample that contains a sugar chain, and into which the carrier of any one of [P1] to [P9] and [P11] above is introduced; and a reagent introduction part that introduces reagents into the container. [P21] The apparatus for concentration of sugar chains of [P20] above, which further includes a solid-liquid separation part that is for solid-liquid separation of contents of the container.

According to the above configuration, it is possible to perform concentration of sugar chains more simply by assembling a carrier and members necessary for concentration of sugar chains.

Advantageous Effects of Invention

According to the present invention, it is possible to provide a technique capable of specifically and efficiently capturing hydrophilic glycopeptides and sugar chains.

DESCRIPTION OF EMBODIMENTS

Figure 1:
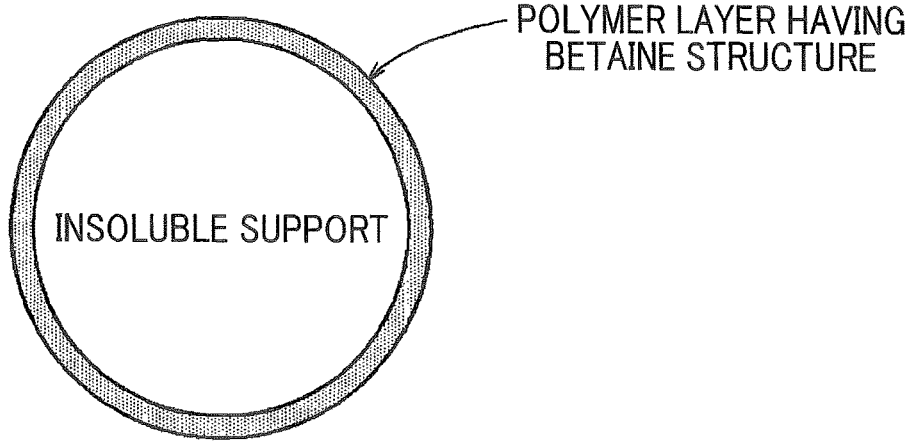
FIG. 1 is a view schematically showing an example of a carrier according to the present embodiment.

Hereinafter, embodiments of the present invention will be described in detail. However, the present invention is not limited to the embodiments to be described later.

[Purification Agent]

In one embodiment, the present invention provides a purification agent which includes a compound having a betaine structure, and which is for a sugar chain having a length equal to or longer than that of a monosaccharide or for a glycopeptide having a sugar chain having a length equal to or longer than that of a monosaccharide. As will be described later in Examples, it is possible to efficiently purify a sugar chain having a length equal to or longer than that of a monosaccharide or a glycopeptide having a sugar chain having a length equal to or longer than that of a monosaccharide with the purification agent of the present embodiment.

The purification agent of the present embodiment can also be said to be a purification agent includes a compound having a betaine structure as an active ingredient, and which is for a sugar chain having a length equal to or longer than that of a monosaccharide or for a glycopeptide having a sugar chain having a length equal to or longer than that of a monosaccharide. In other words, as long as the purification agent of the present embodiment contains a compound having a betaine structure, it is possible to purify a sugar chain having a length equal to or longer than that of a monosaccharide or a glycopeptide having a sugar chain having a length equal to or longer than that of a monosaccharide even when a purification agent is a mixture with a compound not having a betaine structure.

The purification agent of the present embodiment may be immobilized on an insoluble support to form a carrier for purification for a sugar chain having a length equal to or longer than that of a monosaccharide or a glycopeptide having a sugar chain having a length equal to or longer than that of a monosaccharide. In the present specification, the term "carrier for purification" may be simply referred to as the "carrier."

The above-mentioned betaine structure may be a structure represented by Formula (1).

$$—Z\text{-}L\text{-}A \tag{1}$$

(In Formula (1), Z represents a cationic group selected from the group consisting of a secondary amino group, a tertiary amino group, a quaternary ammonium group, and an imino group; L represents an alkylene group having 1 to 10 carbon atoms; and A represents an anionic group selected from the group consisting of a phosphoric acid group, a carboxyl group, a phosphonic acid group, a phosphinic acid group, a sulfonic acid group, a sulfin group, a sulfene group, a hydroxyl group, a thiol group, and a boronic acid group.)

The above-mentioned compound having a betaine structure may be betaine or may be a polymer in which a side chain having a betaine structure is bonded to a main chain.

As will be described later in Examples, the purification agent of the present embodiment has a much higher ability to purify short sugar chains as compared with purification agents of the related art. The term "purification" can also be referred to as the term "concentration."

In the present specification, a main chain refers to the longest carbon chain in a polymer structure, and a structure branched from the main chain is referred to as a side chain. In addition, in the present specification, a sugar chain includes a monosaccharide. Accordingly, a sugar chain having a length equal to or longer than that of a monosaccharide includes a sugar chain having a length equal to or longer than that of a monosaccharide, a disaccharide, a trisaccharide, or a tetrasaccharide. A molecular weight of a sugar chain having a length equal to or longer than that of a monosaccharide may be, for example, about 150 to 3000.

In the carrier according to the embodiment, a polymer is immobilized on an insoluble support, and the polymer is a polymer in which a side chain having a betaine structure is bonded to a main chain. In the carrier according to the embodiment, hydrophilicity is greatly improved by having a betaine structure, and therefore the carrier can strongly hold glycopeptides and sugar chains having high hydrophilicity by hydrophilic interaction.

In the carrier according to the embodiment, a polymer is immobilized on an insoluble support, and preferably, the polymer covers all or a part of a surface of the insoluble support to form a polymer layer. Herein, the term "cover" means that a polymer is attached to a surface of an insoluble support. FIG. 1 schematically shows an example of a carrier according to the present embodiment. In the carrier of FIG. 1, a polymer layer having a betaine structure is formed on a surface of an insoluble support.

A polymer layer may contain a polymer not having a betaine structure, in addition to a polymer in which a side chain having a betaine structure is bonded to a main chain. As long as a betaine structure is present on a surface of the carrier according to the embodiment, it is possible to purify a sugar chain having a length equal to or longer than that of a monosaccharide or a glycopeptide having a sugar chain having a length equal to or longer than that of a monosaccharide.

An insoluble support is a base that is insoluble in water and an organic solvent used in a purification process of sugar chains or glycopeptides, and is not particularly limited as long as the polymer according to the embodiment can be immobilized thereon. A material of the insoluble support may be any of an inorganic substance or an organic substance, or may be a composite substance in which they are used in combination. Examples of inorganic substances include silicon compounds such as silica; glass such as silicate glass; oxides such as iron oxide (ferrite, magnetite, and the like), alumina, titania, and zirconia; metals such as iron, copper, gold, silver, platinum, cobalt, aluminum, palladium, iridium, and rhodium, and alloys of these metals; carbon materials such as graphite; and the like. These may be used alone, or two or more thereof may be used in combination. Examples of organic substances include synthetic polymers such as crosslinked polyvinyl alcohol, crosslinked polyacrylate, crosslinked polyacrylamide, and crosslinked polystyrene; polysaccharides such as crosslinked sepharose, crystalline cellulose, crosslinked cellulose, crosslinked amylose, crosslinked agarose, and crosslinked dextran; and the like. These may be used alone, or two or more thereof may be used in combination. In addition, a polymer itself in which a side chain having a betaine structure is bonded to a main chain may form an insoluble support.

As an insoluble support, it is preferable to use inorganic substances, particularly preferably silicon compounds, and among them, silica is particularly preferable. Generally, an organic substance which can be used as the insoluble support has a specific gravity of about 1, and a difference in specific gravity from a glycopeptide solution and a sugar chain solution is small, and therefore solid-liquid separation often becomes complicated. By using an inorganic substance, for example, in a case where the carrier according to the embodiment is applied for concentration of glycopeptides and sugar chains, and the like, it is possible to easily and easily perform solid-liquid separation, and it is possible to effectively separate glycopeptides and sugar chains captured by the carrier from contaminants such as free peptide fragments. This can contribute to improvement of concentration efficiency. In addition, an inorganic substance can impart an appropriate strength to the carrier.

The insoluble support may have a void such as a porous body or a hollow body.

Examples of porous bodies include monolith-type silica and the like. Monolith-type silica is a porous structure body of silica having a micrometer-sized three-dimensional network-like pore (macropore) and a nanometer-sized pore (mesopore) in a silica skeleton that forms a three-dimensional network-like structure. A pore size of micropores and a pore size of mesopores can be controlled independently within a range of, for example, 1 μm to 100 μm, and preferably 1 μm to 50 μm; and for example, 1 nm to 100 nm, and preferably 1 nm to 70 nm, respectively. By using the insoluble support having such a void, the carrier according to the embodiment can have a large specific surface area, and thus can increase an amount of a purification agent that can be immobilized on a surface of the insoluble support. Accordingly, when the carrier of the embodiment is used to concentrate glycopeptides and sugar chains, contact efficiency with glycopeptides and sugar chains can be improved, and glycopeptides and sugar chains can be captured efficiently, and this can contribute to improvement of concentration efficiency. In addition, it can also be used for adjustment of a specific gravity of an insoluble support to be described later.

When a purification agent is a polymer, the polymer may be a polymer of polymerizable monomers. A polymerizable monomer is not particularly limited as long as it is a monomer capable of forming a polymer by polymerization reaction, and is preferably a (meth)acrylic compound having a (meth)acryloyl group. Examples thereof include a (meth)acrylic ester and derivatives thereof. Examples thereof further include a compound having a vinyl group, an allyl group, an α-alkoxymethyl acryloyl group, a maleic acid residue, a fumaric acid residue, an itaconic acid residue, a crotonic acid residue, an isocrotonic acid residue, and a citraconic acid residue, and derivatives thereof, but examples are not limited thereto. A polymerizable monomer may be used alone or in combination of two or more kinds thereof. A "(meth)acryloyl group" represents an "acryloyl group" or a "methacryloyl group," and "(meth)acryl" represents "acryl" or "methacryl."

A side chain of a polymer immobilized on the insoluble support according to the embodiment is a molecular chain branched from a main chain composed of a polymer of the above-mentioned polymerizable monomers, and has a betaine structure in part or entirety thereof. A betaine structure means a structure having a cationic moiety and an anionic moiety at positions which are separated and non-adjacent in the same molecule.

A cationic moiety is a positively charged atomic group and means a so-called cationic group. Examples of cationic groups include a primary amino group, a secondary amino group (—NHR), a tertiary amino group (—NR$_2$), a quaternary ammonium group (—NR$_3^+$), an imino group, and the like, but examples are not limited thereto. R in a secondary amino group, tertiary amino group, and quaternary ammonium group is an alkyl group or an aryl group, and when there are a plurality of R's in one group, they may be different or the same. Examples thereof include a methyl group, an ethyl group, a propyl group, and the like, but examples are not limited thereto. R is preferably a quaternary ammonium group, and is particularly preferably a trimethyl ammonium group. In addition, cationic groups also include those in the form of salts which form salts with fluoride ion, chloride ion, bromide ion, iodide ion, hydrochloric acid ion, acetic acid ion, sulfuric acid ion, hydrofluoric acid ion, carbonate ion, and the like.

An anionic moiety is a negatively charged atomic group and means a so-called anionic group. Examples of anionic groups include a phosphoric acid group, a phosphonic acid group, a phosphinic acid group, a sulfonic acid group, a sulfin group, a sulfene group, a carboxyl group, a hydroxyl group, a thiol group, a boronic acid group, and the like, but examples are not limited thereto. An anionic group is preferably a phosphoric acid group. In addition, anionic group also include those in the form of salts which form salts with alkali metal ions such as sodium ion and potassium ion, alkaline earth metal ions such as calcium ion, and the like.

A betaine structure is not particularly limited as long as it is a structure having the cationic moiety and the anionic moiety described above, and a combination of the cationic moiety and the anionic moiety is not particularly limited. The cationic moiety is preferably a quaternary ammonium group, and the anionic moiety is preferably a phosphoric acid group.

A polymer immobilized on the insoluble support according to the embodiment is not particularly limited as long as a side chain having a betaine structure is bonded to a main chain composed of a polymer of polymerizable monomers. Accordingly, a polymer may be a homopolymer of polymerizable monomers having a betaine structure, or also may be a copolymer of polymerizable monomers having a cationic moiety and polymerizable monomers having an anionic moiety. In addition, a polymer may be a copolymer containing polymerizable monomers not having charge, and by incorporating such polymerizable monomers, solubility of a polymer in water and the like can be controlled. A copolymer means a polymer obtained from two or more types of monomers, and may be any of an alternating copolymer, a block copolymer, a random copolymer, a graft copolymer, and the like. Accordingly, a betaine structure may be introduced for each monomer unit of a polymer, may be introduced for each constant unit of a monomer unit, or may be randomly introduced.

A polymer side chain is preferably a homopolymer of polymerizable monomers having a betaine structure. In this case, in the polymerizable monomers having a betaine structure, an anionic moiety and a cationic moiety are present in the same molecular chain. A linker that links both moieties is not particularly limited as long as it has a divalent or higher group, and known linkers can be used. An alkylene linker is preferable. Examples of alkylene linkers include an alkylene linker having 1 to 10 carbon atoms, preferably 2 to 5 carbon atoms.

Examples of such polymerizable monomers having a betaine structure include a phosphobetaine-based monomer having a phosphobetaine group such as a phosphorylcholine group, a carboxybetaine-based monomer having a carboxybetaine group, a sulfobetaine-based monomer having a sulfobetaine group, and the like, but examples are not limited thereto. Polymerizable monomer are preferably phosphobetaine-based monomers, and among them, phosphobetaine-based monomers having a phosphorylcholine group are preferable.

As the phosphobetaine-based monomer, a polymerizable monomer having a phosphorylcholine group is preferable, and examples thereof include 2-(meth)acryloyloxyethyl phosphorylcholine, 2-(meth)acryloyloxyethoxyethyl phosphorylcholine, 6-(meth)acryloyloxyhexyl phosphorylcholine, 10-(meth)acryloyloxyethoxynonyl phosphorylcholine, 2-(meth)acryloyloxypropyl phosphorylcholine, 2-(meth) acryloyloxybutyl phosphorylcholine, and the like. Among them, 2-(meth)acryloyloxyethyl phosphorylcholine is particularly preferable from the viewpoint of easy availability. In addition, examples of phosphobetaine-based monomers include dimethyl(2-methacryloyloxyethyl)(2-phosphonatoethyl)aminium, dimethyl(2-acryloyloxyethyl)(2-phosphonatoethyl)aminium, dimethyl(2-methacryloyloxyethyl)(3-phosphonatopropyl)aminium, dimethyl(2-acryloyloxyethyl) (3-phosphonatopropyl)aminium, dimethyl(2-methacryloyloxyethyl)(4-phosphonatobutyl)aminium, dimethyl(2-acryloyloxyethyl)(4-phosphonatobutyl)aminium, dimethyl(2-methacryloyloxyethyl)(phosphonatomethyl)aminium, dimethyl(2-acryloyloxyethyl)(phosphonatomethyl)aminium, and the like.

In addition, examples of carboxybetaine-based monomers include dimethyl(2-methacryloyloxyethyl)(2-carboxylatoethyl)aminium, dimethyl(2-acryloyloxyethyl)(2-carboxylatoethyl)aminium, dimethyl(2-methacryloyloxyethyl)(3-carboxylatopropyl)aminium, dimethyl(2-acryloyloxyethyl) (3-carboxylatopropyl)aminium, dimethyl(2-methacryloyloxyethyl)(4-carboxylatobutyl)aminium, dimethyl(2-acryloyloxyethyl)(4-carboxylatobutyl)aminium, dimethyl(2-methacryloyloxyethyl)(carboxylatomethyl)aminium, dimethyl(2-acryloyloxyethyl)(carboxylatomethyl) aminium, and the like.

In addition, examples of sulfobetaine-based monomers include dimethyl(2-methacryloyloxyethyl)(2-sulfonatoethyl)aminium, dimethyl(2-acryloyloxyethyl)(2-sulfonatoethyl)aminium, dimethyl(2-methacryloyloxyethyl)(3-sulfonatopropyl)aminium, dimethyl(2-acryloyloxyethyl)(3-sulfonatopropyl)aminium, dimethyl(2-methacryloyloxyethyl)(4-sulfonatobutyl)aminium, dimethyl (2-acryloyloxyethyl)(4-sulfonatobutyl)aminium, dimethyl (2-methacryloyloxyethyl)(sulfonatomethyl)aminium, dimethyl(2-acryloyloxyethyl)(sulfonatomethyl)aminium, and the like.

A weight of a polymer bonded to the insoluble support is preferably about 0.5 mg to 1.5 mg per unit surface area ($m^2$) of the insoluble support, and in particular, a weight is preferably 0.6 mg to 1.3 mg, and is more preferably 0.7 mg to 1.2 mg. When a polymer weight per unit surface area is within the above range, handling at the time of polymer synthesis is favorable, and favorable contact efficiency with glycopeptides and sugar chains can be secured, and thus glycopeptides and sugar chains can be captured efficiently.

The carrier according to the embodiment preferably has a specific gravity of about 1.05 to 3.00, and in particular, a specific gravity is preferably 1.1 to 2.7, and is more preferably 1.5 to 2.5. When a specific gravity is less than a lower limit value, sedimentation property decreases, and when a specific gravity exceeds an upper limit value, dispersibility deteriorates, and operability deteriorates in any case. Accordingly, when a specific gravity of the carrier according to the embodiment is within the above range, sedimentation property is favorable in a case where the carrier is applied for concentration of glycopeptides and sugar chains, and the like, and therefore it is possible to easily and simply perform solid-liquid separation by natural sedimentation by gravity, centrifugal separation, or the like, and it is possible to effectively separate glycopeptides and sugar chains captured by the carrier from contaminants such as free peptide fragments. In addition, since dispersibility is favorable, contact efficiency with glycopeptides or sugar chains is improved, and therefore glycopeptides or sugar chains can be efficiently captured. Accordingly, while being able to provide a carrier excellent in terms of operability, it is possible to provide a carrier also excellent in terms of separation from free peptide fragments and the like and of capture efficiency of glycopeptides and sugar chains in a case where the carrier is applied for concentration of glycopeptides and sugar chains, and the like.

A shape of the carrier of the embodiment is not particularly limited, and may be any known shape. Examples thereof include spherical shapes such as beads, plate shapes such as substrates and multi-well plates, film shapes such as sheets, films, and membranes, fiber shapes, and the like. The carrier can also be referred to as a solid phase. A shape thereof is preferably a spherical shape or similar shape, which is easily handled. When a shape is spherical, an average particle diameter is preferably about 0.5 µm to 100 µm, and in particular, is preferably 1 µm to 50 µm, or 1 µm to 10 µm. An average particle diameter is particularly preferably 3 µm to 10 µm. When an average particle diameter is less than a lower limit value, recovery of the carrier by centrifugal separation or filtration becomes difficult, and liquid permeability deteriorates, and it is necessary to apply a large pressure for liquid permeation when the carrier is packed in a column and the like to be used. On the other hand, when an average particle diameter exceeds an upper limit value, a contact area between the carrier and a sample solution decreases, and therefore capture efficiency of glycopeptides and sugar chains decreases, and concentration efficiency decreases. Accordingly, when an average particle diameter of the carrier according to the embodiment is within the above range, while being able to provide a carrier excellent in terms of operability, it is possible to provide a carrier also excellent in terms of separation from free peptide fragments and the like and of capture efficiency of glycopeptides and sugar chains in a case where the carrier is applied for concentration of glycopeptides and sugar chains, and the like. An average particle diameter can be measured with, for example, a particle size distribution analyzer or the like.

The carrier according to the embodiment may be used in a state of being packed in a filter cup such as a spin column, each well of a multiwell plate, each well of a filter plate, a container such as a microtube, and the like.

A polymer can be obtained by polymerizing the above-described polymerizable monomers, but a polymerization method of a polymer is not particularly limited, and can be appropriately selected according to types of polymerizable monomers and the like. A preferable polymerization method is radical polymerization.

Immobilization of a polymer on an insoluble support may be performed using any of physical adsorption or chemical bonding. Chemical bonding is preferable from the viewpoint of stability, and elution of a polymer from an insoluble support can be suppressed. In addition, a polymer may be immobilized on a surface of an insoluble support by polymerizing polymerizable monomers on the surface of the insoluble support, or a polymer polymerized in advance may be immobilized on the surface of the insoluble support.

In a case of immobilizing a polymer on a surface of an insoluble support by polymerizing polymerizable monomers on the surface of the insoluble support, for example, a polymerization initiation point is introduced on the surface of the insoluble support, the insoluble support in which the polymerization initiation point introduced is immersed in a polymerizable monomer solution, and a polymer is grown from the polymerization initiation point by adding a polymerization initiator. Accordingly, it is possible to immobilize a polymer on a surface of an insoluble support by chemical bonding. As a polymerization initiation point, polymerizable functional groups, chain transfer groups, dormant species in living radical polymerization, and the like can be used.

Examples of polymerizable functional groups include a vinyl group, an allyl group (a 2-propenyl group), a (meth) acryloyl group, an epoxy group, a styrene group, and the like. Examples of chain transfer groups include a mercapto group, an amino group, and the like, but a mercapto group is preferable from the viewpoint of being excellent in reactivity.

A method for introducing a polymerizable functional group or a chain transfer group on a surface of an insoluble support is not particularly limited, but it is preferable to use a silane coupling agent having a polymerizable functional group or a chain transfer group.

Examples of silane coupling agents having a polymerizable functional group include (3-methacryloxypropyl)dimethylmethoxysilane, (3-methacryloxypropyl)diethylmethoxysilane, (3-methacryloxypropyl)dimethylethoxysilane, (3-methacryloxypropyl)diethylethoxysilane, (3-methacryloxypropyl)methyldimethoxysilane, (3-methacryloxypropyl)ethyldimethoxysilane, (3-methacryloxypropyl)methyldiethoxysilane, (3-methacryloxypropyl)ethyldiethoxysilane, (3-methacryloxypropyl)trimethoxysilane, (3-methacryloxypropyl)triethoxysilane, and the like, but (3-methacryloxypropyl)trimethoxysilane or (3-methacryloxypropyl)triethoxysilane is preferable from the viewpoint of reactivity and availability. These silane coupling agents can be used alone or in combination of two or more kinds thereof.

Examples of silane coupling agents having a chain transfer group include (3-mercaptopropyl)trimethoxysilane, (3-mercaptopropyl)methyldimethoxysilane, (3-mercaptopropyl)dimethylmethoxysilane, (3-mercaptopropyl)triethoxysilane, (3-mercaptopropyl)methyldiethoxysilane, (3-mercaptopropyl)dimethylethoxysilane, (mercaptomethyl)trimethoxysilane, (mercaptomethyl)methyldimethoxysilane, (mercaptomethyl)dimethylmethoxysilane, (mercaptomethyl)triethoxysilane, (mercaptomethyl)methyldiethoxysilane, (mercaptomethyl)dimethylethoxysilane, and the like, but (3-mercaptopropyl)trimethoxysilane or (3-mercaptopropyl)triethoxysilane is preferable from the viewpoint of availability. These silane coupling agents can be used alone or in combination of two or more kinds thereof.

Introduction of a polymerizable functional group or a chain transfer group into an insoluble support using a silane coupling agent having a polymerizable functional group or a chain transfer group can be performed by, for example, forming a covalent bond between the silane coupling agent and the functional group on a surface of an insoluble support. For example, in a case of using alkoxysilanes such as trimethoxysilanes and triethoxysilanes as a silane coupling agent, introduction can be performed by dehydration and condensation of a silanol group with a hydroxyl group, an amino group, a carbonyl group, a silanol group, or the like on a surface of an insoluble support to form a covalent bond.

After introducing a polymerizable functional group or a chain transfer group on a surface of an insoluble support, a polymer layer is formed on the surface of the insoluble support by mixing the insoluble support and the polymerizable monomers and proceeding the polymerization reaction. A polymerization reaction is not limited, but is performed by, for example, inputting an insoluble support to a solvent in which polymerizable monomers and a polymerization initiator are dissolved and heating at a temperature of 0° C. to 80° C. for 1 hour to 30 hours while stirring. Thereafter, the insoluble support is filtered under reduced pressure, washed, and then dried.

A use ratio of an insoluble support to a polymerizable monomer and a polymerization initiator is not particularly limited, but is generally a use ratio of 0.1 mmol to 10 mmol of polymerizable monomers, and 0.01 mmol to 10 mmol of a polymerization initiator with respect to 1 g of an insoluble support.

Any solvent may be used as long as it dissolves the respective polymerizable monomer, and examples thereof include alcohols such as methanol, ethanol, isopropanol, n-butanol, t-butyl alcohol, and n-pentanol, benzene, toluene, tetrahydrofuran, dioxane, dichloromethane, chloroform, cyclohexanone, N,N-dimethylformamide, dimethyl sulfoxide, methyl acetate, ethyl acetate, butyl acetate, methyl ethyl ketone, methyl butyl ketone, ethylene glycol monoethyl ether, ethylene glycol monomethyl ether, ethylene glycol monobutyl ether, and the like. These solvents may be used alone or in combination of two or more kinds thereof.

A polymerization initiator is not particularly limited. For example, it is possible to use azo compounds such as 2,2'-azobisisobutyl nitrile (hereinafter abbreviated as "AIBN" in some cases) and 1,1'-azobis(cyclohexane-1-carbonitrile); organic peroxides such as benzoyl peroxide, lauryl peroxide, and tert-butyl peroxide; redox initiators such as hydrogen peroxide-ferrous ion; and the like.

Meanwhile, when immobilizing a polymer polymerized in advance on a surface of an insoluble support, there is a method of physically adsorbing a polymer polymerized in advance to an insoluble support, or a method of chemically bonding. In a polymer, a component that is easily adsorbed to an insoluble support, or a component that has a functional group capable of reacting with a reactive functional group present on a surface of an insoluble support is preferably incorporated as a copolymer at the time of polymerization of the polymer. For example, as a functional group capable of reacting with a reactive functional group present on a surface of an insoluble support, for example, a silanol group obtained by hydrolyzing a silane coupling agent, and the like is preferable because it has high reactivity, and a covalent bond can be formed by dehydration and condensation of a silanol group with a hydroxyl group, an amino group, a carbonyl group, a silanol group, or the like on a surface of a solid support. A polymerization reaction of polymerizable monomers can be carried out as described above.

By applying the above-mentioned polymer to a surface of an insoluble support, the polymer can be adsorbed or chemically bonded to the surface of the insoluble support. Examples of application methods include known methods in which a solution of a polymer is prepared, and immersion and spraying are performed; and the like. After application, drying is preferably performed at room temperature or under heating. In a case of chemical bonding, application may be carried out under reaction conditions appropriate to each case. Accordingly, a polymer layer is formed on a surface of an insoluble support.

Figure 2:
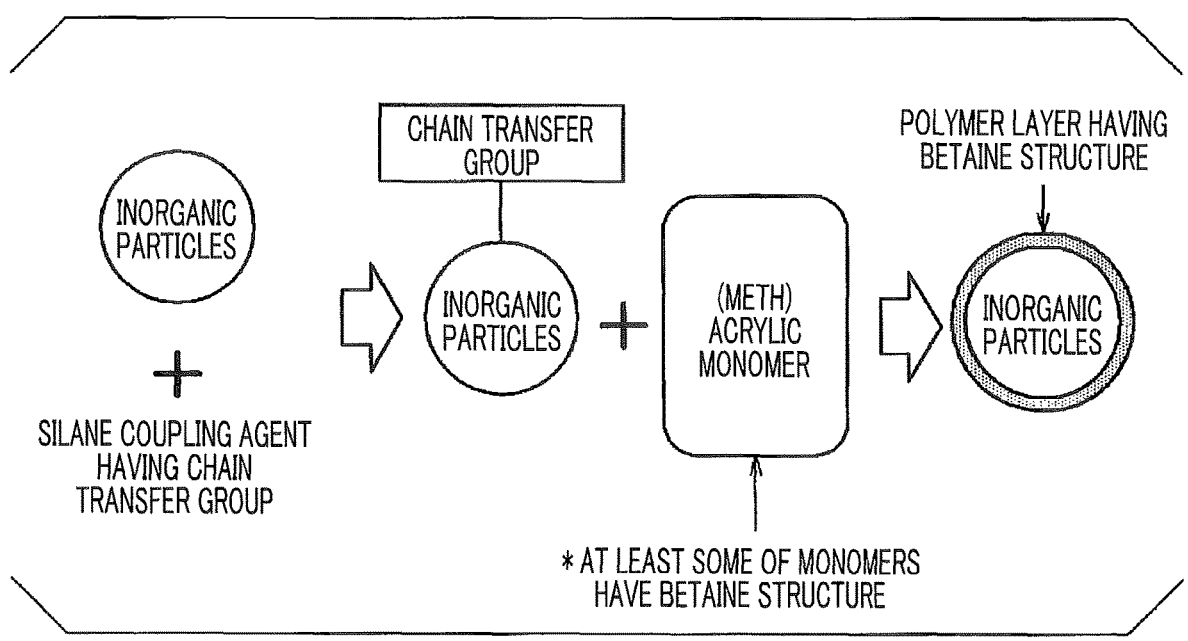
FIG. 2 is a view schematically showing an example of a method of synthesizing a polymer layer of a carrier according to the present embodiment.

FIG. 2 schematically shows an example of a method of synthesizing a polymer layer of a carrier according to the present embodiment. The carrier shown in FIG. 2 is a carrier in which a chain transfer group such as a mercapto group is introduced on a surface of an inorganic particle having a hydroxyl group on a surface thereof, such as a silica bead as an insoluble support, and thereby a polymer layer containing a betaine structure is synthesized. First, a chain transfer group is introduced to a surface of an inorganic particle using a silane coupling agent having a chain transfer group. At this time, a silanol group generated by hydrolysis of a hydrolyzable group such as an alkoxy group of a silane coupling agent is dehydrated and condensed with a hydroxyl group on the surface of the inorganic particle to form a covalent bond, thereby a chain transfer group is introduced. Subsequently, an inorganic particle in which a chain transfer group is introduced, and a (meth)acrylic monomer in which at least a part of the monomer has a betaine structure are radically polymerized by adding a polymerization initiator under an appropriate solvent. The chain transfer group introduced to the inorganic particle serves as a polymerization initiation point, and a surface of the inorganic particle is coated with a polymer layer having a betaine structure, and thereby a polymer layer is formed.

(Use Applications of Purification Agent)

1. Concentration of Glycopeptide

The purification agent according to the present embodiment can be suitably used for concentration of glycopeptides, and in order to specifically capture glycopeptides, contaminants such as free peptide fragments having no sugar chain are removed, and glycopeptides can then be concentrated. Herein, the term "concentration" means increasing a concentration and abundance ratio of glycopeptides compared to before concentration, and includes meaning of, for example, selectively recovering a glycopeptide from a sample in which glycopeptides such as degradation products of glycoproteins and contaminants such as free peptide fragments are mixed.

A glycopeptide is a glycopeptide in which a part of amino acids constituting a peptide is bonded to a sugar chain in which one or more monosaccharides or derivatives thereof, or two or more monosaccharides and/or derivatives thereof are linked in a linear or branched form by a glycosidic bond, and the purification agent according to the present embodiment targets all glycopeptides for concentration. A sugar chain of a glycopeptide is broadly classified into mainly two types: N-glycosidic bonded sugar chains (N-type sugar chains) in which sugar chains are bonded to asparagine residues, and O-glycosidic bonded sugar chains (O-type sugar chains) in which sugar chains are bonded to serine and threonine. The purification agent according to the present embodiment targets any glycopeptide for concentration, and types, chain lengths, structures, and the like of glycopeptides are not particularly limited. Accordingly, even regarding a glycopeptide having an O-bonding type sugar chain with a small molecular weight and a glycopeptide having a long peptide region, it is possible to specifically and efficiently concentrate a glycopeptide by minimizing an influence of contaminants such as free peptide fragments and peptides such as peptide regions of glycopeptides, which are present in large amounts.

2. Concentration of Sugar Chain

The purification agent according to the present embodiment can be suitably used for concentration of sugar chains, and in order to specifically capture sugar chains, contaminants other than sugar chains (proteins, peptides, lipids, salts, and the like) are removed to concentrate sugar chains. Herein, the term "concentration" means increasing a concentration and abundance ratio of sugar chains compared to before concentration, and includes meaning of, for example, selectively recovering a sugar chain from a sample in which sugar chains released from glycoproteins and contaminants such as free peptide fragments are mixed.

A sugar chain is a compound in which one or more monosaccharides or derivatives thereof, or two or more monosaccharides and/or derivatives thereof are linked in a linear or branched form by a glycosidic bond, and the carrier according to the embodiment targets all sugar chains for concentration. Examples of monosaccharides constituting a sugar chain or derivatives thereof include glucose, galactose, mannose, fucose, xylose, N-acetylglucosamine, fucose, sialic acid, arabinose, and the like, and derivatives thereof. Examples of sugar chains include monosaccharides and derivatives thereof, polysaccharides, glycoproteins; sugar chains released or induced from complex carbohydrates such as glycopeptides, proteoglycans, and glycolipids; and the like, but examples are not limited thereto. In particular, the carrier according to the embodiment can efficiently concentrate small sugars such as monosaccharides and disaccharides. Herein, a sugar chain constituting a glycoprotein is broadly classified into mainly two types: N-glycosidic bonded sugar chains (N-type sugar chains) in which sugar chains are bonded to asparagine residues, and O-glycosidic bonded sugar chains (O-type sugar chains) in which sugar chains are bonded to serine and threonine. The carrier according to the embodiment targets any sugar chain for concentration, and types, chain lengths, structures, and the like of sugar chains are not particularly limited. Accordingly, it is possible to effectively concentrate O-bonding type sugar chains with a small molecular weight and the like by minimizing an influence of impurities (proteins, peptides, lipids, salts, and the like) other than sugar chains which are present in large amounts.

[Method for Concentrating Glycopeptides]

In one embodiment, the present invention provides a method for purifying a glycopeptide having a sugar chain having a length equal to or longer than that of a monosaccharide, the method including brining the above-described purification agent into contact with a sample containing a glycopeptide having a sugar chain having a length equal to or longer than that of a monosaccharide and containing an organic solvent to adsorb the glycopeptide having a sugar chain having a length equal to or longer than that of a monosaccharide to the purification agent; and bringing the purification agent into contact with water to elute the glycopeptide having a sugar chain having a length equal to or longer than that of a monosaccharide.

A method for concentrating a glycopeptide according to the present embodiment includes a step of concentrating a glycopeptide using the purification agent according to the embodiment. In more detail, the method is for concentrating a glycopeptide from a sample containing the glycopeptide, and since the purification agent according to the embodiment has a significantly improved hydrophilicity, the purification agent has affinity to a glycopeptide having a higher hydrophilicity as compared to a peptide. On the other hand, since a peptide is less hydrophilic than a glycopeptide, affinity of the purification agent according to the embodiment with respect to the peptide is low. Accordingly, the purification agent according to the embodiment can specifically and efficiently capture and concentrate glycopeptides. The method for concentrating glycopeptides according to the present embodiment targets any glycopeptides described above for concentration.

A sample containing a glycopeptide is not particularly limited as long as it is a sample that probably contains a glycopeptide, and examples thereof include samples obtained by subjecting samples containing a glycoprotein to a fragmentation treatment of glycoproteins. The sample containing a glycoproteins is a biological sample, an environmental sample, and the like, and examples thereof include biological samples such as whole blood, serum, plasma, urine, saliva, feces, cerebrospinal fluid, cells and cell cultures, tissues, and the like. A biological sample may be unpurified, may be a sample obtained by purifying a glycoprotein by a known technique, or may be a sample subjected to a treatment such as degreasing, desalting, and protein fractionation.

A fragmentation process of glycoproteins is not particularly limited as long as it can fragment a protein part of glycoproteins, and can be performed by using a protease or the like. Examples thereof include trypsin, chymotrypsin, pepsin, V8 protease, pronase, proteinase K, lysyl endoprotease, promelain, thermolysin, ficin, caspase, subtilisin, and the like.

Glycoproteins in a sample may be denatured or reduced prior to protease treatment to facilitate cleavage by a protease. Examples of modifiers include surfactants, chaotropic agents, and the like; and examples of reducing agents include β-mercaptoethanol, dithiothreitol, glutathione, tris-2-carboxyethyl phosphine, tributyl phosphine, and the like, bur examples are not limited thereto.

In the method for concentrating a glycopeptide according to the present embodiment, first, a sample containing a glycopeptide is brought into contact with the purification agent according to the embodiment, and the carrier captures the glycopeptide. The purification agent according to the embodiment is improved in hydrophilicity, and thus can specifically capture a glycopeptide by hydrophilic interaction, and large amounts of peptide fragments and the like present in a sample are not captured by the carrier and remain a free state.

Holding power with respect to a glycopeptide by the purification agent according to the embodiment is proportional to a concentration of an organic solvent. Therefore, an organic solvent or a mixed solvent of an organic solvent and water can be used as a solvent of a reaction liquid when the purification agent captures a glycopeptide. The solvent can be appropriately selected depending on the type and the like of a glycopeptide that is a concentration target. The organic solvent is not particularly limited as long as it can dissolve a glycopeptide. Examples thereof include acetonitrile, tetrahydrofuran, acetone, dioxane, pyridine, methanol, ethanol, 1-propanol, 2-propanol, 1-butanol, and the like. Preferably, an organic solvent such as 1-butanol or ethanol is suitably used. Various buffer solutions can be used for pH adjustment. In addition, when a mixed solvent of an organic solvent and water is used, a mixing ratio of the organic solvent to water is, for example, 3:1 to 10:1 in volume ratio.

Subsequently, if necessary, the purification agent captured a glycopeptide is washed. The purification agent is preferably immobilized on an insoluble support. By washing, substances other than the glycopeptide captured on the carrier, in particular, free peptide fragments can be removed. For example, the above-described solvent can be used as the washing solution.

After washing, the glycopeptide can be specifically concentrated by releasing the glycopeptide from the carrier that captured the glycopeptide.

As an eluate for releasing the glycopeptide, it is possible to use an organic solvent or a mixed solvent of an organic solvent and water, and an eluate can be appropriately selected according to the type of a glycopeptide or a polymer that is a concentration target. As the organic solvent, examples described above can be used. In addition, in the present step, the glycopeptide can be efficiently released by using a solvent having high hydrophilicity. For example, water can be used alone without using an organic solvent, or a mixed solvent of an organic solvent and water can be used. When using a mixed solvent, an organic solvent is 3 times or less water in volume ratio, for example.

A method for concentrating glycopeptides according to the present embodiment can be carried out by selecting a known concentration form that uses a carrier. Examples include a batch method, a spin column method, and the like, but examples are not limited thereto. The batch method and the spin column method will be described in detail, but the reagents, reaction conditions, and the like are as described above.

(Batch Method)

In the case of concentration by a batch method, a sample containing a glycopeptide and the purification agent according to the embodiment are immersed in a reaction liquid in a suitable container (for example, a microtube, a centrifuge tube, a microplate, or the like) so that the purification agent captures the glycopeptide. The purification agent is preferably immobilized on an insoluble support. Subsequently, the carrier-glycopeptide complex is subjected to solid-liquid separation, a liquid phase portion containing contaminants such as free peptide fragments is removed, and the carrier is recovered. Solid-liquid separation can be performed by natural sedimentation by gravity, centrifugal separation, or the like, and the liquid phase portion can be removed by suction or the like. Alternatively, solid-liquid separation may be performed by incorporating a magnetic material such as ferrite into the insoluble support of the carrier, and accumulating the carrier using magnetic force. In this case, centrifugal separation or the like is not required to be carried out. Alternatively, solid-liquid separation may be performed by filtration through a filter, and in that case, it may be performed under reduced pressure or under pressure.

Subsequently, the carrier captured the glycopeptide is washed. By washing, contaminants other than the glycopeptide captured on the carrier, in particular, free peptide fragments can be removed. The washing can be carried out by immersing the carrier that captured the glycopeptide in the washing solution in the above-mentioned appropriate container and repeating exchange of the washing solution. For example, washing can be carried out by repeating the operation of putting a carrier captured a glycopeptide in an appropriate container, adding a washing solution, shaking or stirring, and then removing a liquid phase portion by solid-liquid separation. Solid-liquid separation can be performed as described above.

After washing, the glycopeptide is released from the carrier that captured the glycopeptide.

The release of the glycopeptide can be carried out by immersing the carrier in an eluate. For example, after the washing solution is sufficiently removed, an appropriate amount of eluate is added to the carrier that captured a glycopeptide, and shaken or stirred. Subsequently, the carrier is recovered by solid-liquid separation, and the eluate is collected in a new appropriate container (for example, a collection tube, a collection plate, or the like). Solid-liquid separation can be performed as described above. The glycopeptide can be concentrated by distilling off the eluate if necessary.

(Spin Column Method)

In the case of concentration by a spin column method, concentration can be carried out by using a container containing a filter or the like therein, for example, a filter cup or the like. As the filter cup, for example, it is possible to use filter cups having opening portions at the top and bottom part, in which the opening portion at the bottom part is covered with a filter. In the case of using a filter cup, a sample solution containing a glycopeptide is input to a filter cup filled with the purification agent according to the embodiment, the solution is allowed to pass through, and thereby the carrier is brought into contact with the sample under a reaction liquid. The purification agent is preferably immobilized on an insoluble support. The solution may be allowed to pass through by natural sedimentation by gravity, centrifugal separation, or the like, and may be allowed to pass through under reduced pressure or under pressure. After allowing the solution to pass through, a drained fluid containing the free peptide fragments and the like which have passed through the carrier is removed.

Subsequently, the carrier captured the glycopeptide is washed. By washing, contaminants other than the glycopeptide captured on the carrier, in particular, free peptide fragments can be removed. The washing can be performed by the carrier allowing the washing solution to pass through in the filter cup, and washing can be performed continuously from a glycopeptide capture reaction. Allowing the solution to pass through can be performed as described above.

After washing, the glycopeptide is released from the carrier that captured the glycopeptide. The glycopeptide can be released by the carrier allowing the eluate to pass through in the filter cup, and can be performed continuously from a glycopeptide capture reaction through the washing operation. The eluate after allowing the eluate to pass through by the carrier is collected in an appropriate container (for example, a collection tube, a collection plate, or the like). Allowing the solution to pass through can be performed as described above. The glycopeptide can be concentrated by distilling off the eluate if necessary.

The glycopeptide concentrated by the method for concentrating glycopeptides according to the present embodiment can be used as it is for analysis means such as structural analysis of glycopeptides.

[Method for Concentrating Sugar Chains]

In one embodiment, the present invention provides a method for purifying a sugar chain having a length equal to or longer than that of a monosaccharide, the method including brining the above-described purification agent into contact with a sample containing a sugar chain having a length equal to or longer than that of a monosaccharide and containing an organic solvent to adsorb the sugar chain having a length equal to or longer than that of a monosaccharide to the purification agent; and bringing the purification agent into contact with water to elute the sugar chain having a length equal to or longer than that of a monosaccharide.

A method for concentrating a sugar chain according to the present embodiment includes a step of concentrating a sugar chain using the purification agent according to the present embodiment. In more detail, the method is for concentrating a sugar chain from a sample containing the sugar chain, and since the purification agent according to the present embodiment has significantly improved hydrophilicity, the purification agent has affinity to a sugar chain having higher hydrophilicity than that of a peptide, lipid, or the like. On the other hand, since a peptide, lipid, or the like has lower hydrophilicity than that of a sugar chain, affinity thereof to the purification agent according to the present embodiment is low. Accordingly, the purification agent according to the present embodiment can specifically and efficiently capture and concentrate sugar chains. The method for concentrating a sugar chain according to the present embodiment targets any sugar chains described above for concentration.

The sample containing a sugar chain is not particularly limited as long as it is a sample that probably has a sugar chain, and examples thereof include a sample obtained by hydrolysis treatment of polysaccharides, and a sample obtained by subjecting a sample containing complex carbohydrates such as glycoproteins to sugar chain release treatment and the like, in addition to samples containing sugar chains themselves such as monosaccharides and polysaccharides. A sample containing complex sugar chains such as monosaccharides, polysaccharides, and glycoproteins is a biological sample, an environmental sample, and the like, and examples thereof include biological samples such as whole blood, serum, plasma, urine, saliva, feces, cerebrospinal fluid, cells and cell cultures, and tissues. The biological sample may be an unpurified sample; may be a sample obtained by purifying complex saccharides such as monosaccharides, polysaccharides, and glycoproteins by a known technique; or may be a sample subjected to treatment such as degreasing, desalting, protein fractionation, and heat denaturation.

The sugar chain release treatment from complex saccharides such as glycoproteins is not particularly limited as long as it can release sugar chains from complex saccharides, and any treatment such as enzymatic treatment and chemical treatment may be used. The treatment can be performed by, for example, peptide N-glycanase (PNGase F, PNGase A) digestion, endo-β-N acetylglucosaminidase (Endo-H, Endo-F, Endo-A, Endo-M) digestion, endo-O-glycanase digestion, hydrazine decomposition, trifluoroacetic acid decomposition, (β) elimination by alkali treatment, and the like, but examples are not limited thereto. In addition, prior to the sugar chain release treatment, fragmentation treatment or the like of the protein and the peptide part may be performed on the glycoprotein, glycopeptide, or the like with the above-mentioned protease or the like.

In the method for concentrating sugar chains according to the present embodiment, first, a sample containing sugar chains is brought into contact with the purification agent according to the embodiment, and the purification agent captures the sugar chains. The purification agent is preferably immobilized on an insoluble support. The carrier according to the present embodiment is improved in hydrophilicity, and thus can specifically capture a sugar chain by hydrophilic interaction, and large amounts of contaminants (proteins, peptides, lipids, salts, and the like), which are other than sugar chains and which are present in a sample, are not captured by the carrier and remain a free state.

Holding power with respect to a sugar chain by the carrier according to the present embodiment is proportional to a concentration of an organic solvent. Therefore, an organic solvent or a mixed solvent of an organic solvent and water can be used as a solvent of a reaction liquid when the carrier captures a sugar chain. The solvent can be appropriately selected depending on the type and the like of a sugar chain that is a concentration target. The organic solvent is not particularly limited as long as it can dissolve a sugar chain. Examples thereof include acetonitrile, tetrahydrofuran, acetone, dioxane, pyridine, methanol, ethanol, 1-propanol, 2-propanol, 1-butanol, and the like. Preferably, an organic solvent such as acetonitrile, 1-butanol, or ethanol is suitably used. Various buffer solutions can be used for pH adjustment. In addition, when a mixed solvent of an organic solvent and water is used, a mixing ratio of the organic solvent to water is, for example, 50:50 to 100:0, is preferably 90:10 to 100:0, and is more preferably 95:5 to 100:0 in volume ratio.

Subsequently, if necessary, the carrier captured a sugar chain is washed. By washing, contaminants (proteins, peptides, lipids, salts, and the like) which are other than sugar chains and which are captured by the carrier can be removed. For example, the above-described solvent can be used as the washing solution.

After washing, the sugar chain can be specifically concentrated by releasing the sugar chain from the carrier that captured the sugar chain.

As an eluate for releasing the sugar chain again, it is possible to use an organic solvent or a mixed solvent of an organic solvent and water, and an eluate can be appropriately selected according to the type of a sugar chain or a polymer that is a concentration target. As the organic solvent, examples described above can be used. In addition, in the present step, the sugar chain can be efficiently released by using a solvent having high hydrophilicity. For example, water can be used alone without using an organic solvent, or a mixed solvent of an organic solvent and water can be used. When a mixed solvent is used, an organic solvent is 3 times or less water in volume ratio, for example, but particularly preferably, only water can be used without using an organic solvent.

A method for concentrating sugar chains according to the present embodiment can be carried out by selecting a known concentration form that uses a carrier. Examples include a batch method, a spin column method, and the like, but examples are not limited thereto. The procedures of the batch method and the spin column method can be performed according to the procedure of the above-mentioned [Method for concentrating glycopeptides], and the reagents, reaction conditions and the like are as described above.

The sugar chains concentrated by the sugar chain concentration method according to the present embodiment can be used as they are for analysis means such as structural analysis of sugar chains, and can be labeled if necessary.

[Kit for Concentration of Glycopeptides]

A kit for concentration of glycopeptides according to the present embodiment includes the purification agent according to the embodiment, a protocol for using the kit, and the like as instructions for use. The purification agent is preferably immobilized on an insoluble support. The instructions may be written or printed on paper or other media, or may be recorded on electronic media such as magnetic tape, magnetic disk, optical disk, and the like. As described above, reagents necessary for carrying out the method for concentrating glycopeptides can be provided as a kit.

The kit for concentration of glycopeptides according to the present embodiment can further include reagents and containers necessary for carrying out the kit. Examples thereof include a reaction liquid for capturing a glycopeptide by the carrier according to the present embodiment, a buffer solution for adjusting pH and the like during the reaction, a washing solution for washing, an eluate for releasing glycopeptides from the carrier that captured the glycopeptides, and the like. These may be provided in the form of a lyophilised powder, and in this case, the kit for concentration of glycopeptides may additionally contain a dilution for dilution in use. In addition, containers, such as a filter cup, a multiwell plate, a filter plate, and a microtube may be contained, and the carrier according to the present embodiment may be contained in these containers in the charged state. The definition of each term and the preferred embodiment are as described above. As described above, concentration of glycopeptides can be performed more simply by kitting carriers, reagents, information, and the like necessary for concentration of glycopeptides.

[Kit for Concentration of Sugar Chains]

A kit for concentration of sugar chains according to the present embodiment includes the purification agent according to the embodiment, a protocol for using the kit, and the like as instructions for use. The purification agent is preferably immobilized on an insoluble support. The instructions may be written or printed on paper or other media, or may be recorded on electronic media such as magnetic tape, magnetic disk, optical disk, and the like. As described above, reagents necessary for carrying out the method for concentrating sugar chains can be provided as a kit.

The kit for concentration of sugar chains according to the present embodiment can further include reagents and containers necessary for carrying out the kit. Examples thereof include a reaction liquid for capturing sugar chains by the carrier according to the present embodiment, a buffer solution for adjusting pH and the like during the reaction, a washing solution for washing, an eluate for releasing sugar chains again from the carrier that captured the sugar chains, and the like. These may be provided in the form of a lyophilised powder, and in this case, the kit for concentration of sugar chains may additionally contain a dilution for dilution in use. In addition, containers, such as a filter cup, a multiwell plate, a filter plate, and a microtube may be contained, and the carrier according to the present embodiment may be contained in these containers in the charged state. The definition of each term and the preferred embodiment are as described above. As described above, concentration of sugar chains can be performed more simply by kitting carriers, reagents, information, and the like necessary for concentration of sugar chains.

[Apparatus]

In one embodiment, the present invention provides an apparatus for purification of a sugar chain having a length equal to or longer than that of a monosaccharide or a glycopeptide having a sugar chain having a length equal to or longer than that of a monosaccharide, the apparatus including: a container holding part that holds a container containing the purification agent; and a reagent introduction part that introduces a reagent into the container. The purification agent is preferably immobilized on an insoluble support.

Figure 9:
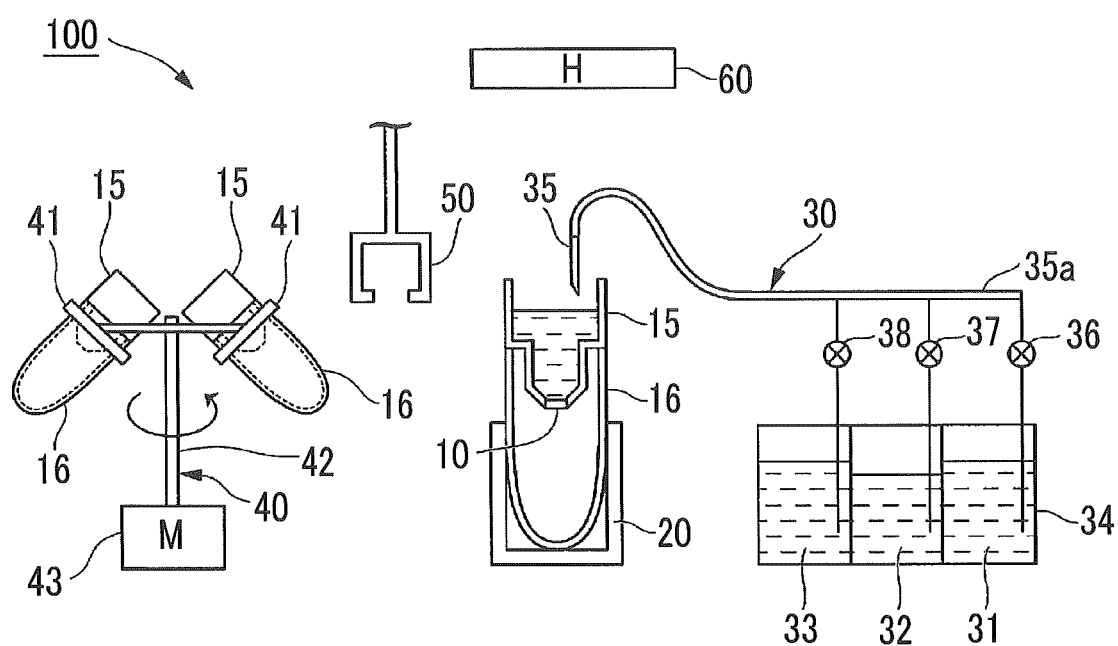
FIG. 9 is a schematic view showing an apparatus for purification of a sugar chain or a glycopeptide according to the present embodiment.

FIG. 9 is a schematic view for explaining the apparatus of the present embodiment. A configuration of the apparatus described below is merely an example, and the apparatus of the present embodiment is not limited to this configuration. As shown in FIG. 9, an apparatus 100 includes a container holding part 20 for holding a container 15 containing a carrier 10 and a reagent introduction part 30 for introducing a reagent into the container 15. In the example of FIG. 9, the container 15 is attached to a recovery container 16 (for example, a collection tube, a collection plate, and the like) to be described later.

The reagent introduction part 30 includes a sample introduction part 35 for introducing a sample 31 containing an organic solvent and a sugar chain having a length equal to or longer than that of a monosaccharide or a glycopeptide having a sugar chain having a length equal to or longer than that of a monosaccharide into the container 15; a washing solution introduction part 35 for introducing a washing solution 32 into the container 15; and an eluate introduction part 35 for introducing an eluate 33 into the container 15. In the present embodiment, the sample introduction part, the washing solution introduction part, and the eluate introduction part are constituted by the same member 35.

The container holding part 20 is for holding the container 15 containing the carrier 10. The container holding part 20 may hold the container 15 directly or may hold another member (recovery container 16) for holding the container 15 as shown in FIG. 9. An aspect in which the container holding part 20 holds the container 15 is not limited to this, and for example, a holding hole or a holding hole of the container holding part 20 may be fitted with most of the container for holding, may be adopted. In addition to this, an aspect in which an engaged projected portion (an engaged recessed portion) of the container is engaged with an engaged recessed portion (an engaged projected portion) of the container and held; an aspect in which the container is held and held by the holding portion of the container holding part; and the like may be adopted.

The reagent introduction part 30 is for introducing liquids into the container 15 held by the container holding part 20. In the example of FIG. 9, the reagent introduction part 30 includes a tank 34 containing the sample 31, the washing solution 32, and the eluate 33, a liquid sending pipe 35a for feeding each reagent contained in the tank 34, valves (36, 37, 38) for controlling sending liquids of each reagent, and the introducing part 35 for introducing each reagent into the interior of the container 15.

The sample introduction part 35, the washing solution introduction part 35, and the eluate introduction part 35 are added with the sample 31, the washing solution 32, and the eluate 33 into the same reaction container 15. An aspect in which the reagent introduction part 30 introduces the liquid into the reaction container 15 is not particularly limited. Examples thereof include an aspect in which the liquid is fed into the container 15 via a tubular member from the liquid sending sources (31, 32, 33) in which the liquid to be sent is stored. In addition to this, the aspect in which a liquid collected in the tubular member is poured into the reaction container, and the like may be adopted.

The apparatus 100 may further include a solid-liquid separation part 40 that solid-liquid separates the contents of the container 15. When the apparatus 100 includes the solid-liquid separation part 40, the solid-liquid separation part 40 separates solid and liquid from the contents contained in the container 15. The solid is a substance that is left in the container 15 and is essentially a substance that is the carrier 10 and a substance that is fixed thereto. In addition, the recovery container 16 (for example, a collection tube, a collection plate, and the like) may be attached to the container 15.

A specific separation system of the solid-liquid separation part 40 is not particularly limited, and examples thereof include centrifugal separation, pressure reduction, pressurization, and the like. In the example of FIG. 9, a separation system of the solid-liquid separation part 40 is centrifugal separation. The solid-liquid separation part 40 includes a rack 41 that holds the container 15 (or 16), a drive shaft 42, and a motor 43.

As in the example of FIG. 9, the solid-liquid separation part 40 may be configured as a component independent of the container holding part 20. In this case, the apparatus 100 may include a container transfer part 50 that automatically transfers the container 15 (and 16) from the container holding part 20 to the solid-liquid separation part 40. The container transfer part 50 may be configured to transfer only the container 15 in transferring the container 15 (and 16), or may be configured to be transferred in a state where the container 15 is attached with the recovery container 16. The container transfer part 50 has an arm operable to grip and open and move the container 15 directly or indirectly (that is, via the recovery container 16), and may be configured with an arm control unit for controlling the operation of the arm.

By operating the solid-liquid separation part 40, a sugar chain having a length equal to or longer than that of a monosaccharide or a glycopeptide having a sugar chain having a length equal to or longer than that of a monosaccharide which is fixed to the carrier 10 can remain in the container 15 by centrifugal separation, decompression, pressurization, and the like, and the washing solution can be discarded into the recovery container 16. In addition, in an elution process, an eluate containing a sugar chain having a length equal to or longer than that of a monosaccharide or a glycopeptide having a sugar chain having a length equal to or longer than that of a monosaccharide can be recovered in the recovery container 16.

The apparatus 100 may further include a temperature regulation part 60 that controls the temperature of the contents of the container 15. When the apparatus 100 includes the temperature regulation part 60, the temperature regulation part 60 may have at least a heater function.

The apparatus 100 may automatically control at least one or preferably all of the operable components (for example, the liquid transfer part 35, the arm 50, the solid-liquid separation part 40, the temperature regulation part 60, and the liquid transfer part 50). As a result, it is possible to more rapidly purify a sugar chain having a length equal to or longer than that of a monosaccharide or a glycopeptide having a sugar chain having a length equal to or longer than that of a monosaccharide.

EXAMPLES

Hereinafter, the present invention will be specifically described in reference to examples. However, the present invention is not limited to these examples.

Synthesis Example (Carrier in which Polymer Containing Structural Unit Derived from 2-Methacryloyloxyethyl Phosphorylcholine is Immobilized on Silica Bead)

The present synthesis example illustrates synthesis of a polymer containing a structural unit derived from 2-methacryloyloxyethyl phosphorylcholine (hereinafter referred to as the "MPC polymer") on a surface of a silica bead as an example, but the example is not intended to limit the scope of the present invention.

Introduction of Chain Transfer Group to Silica Bead 5 g of (3-mercaptopropyl)trimethoxysilane (M0928 manufactured by Tokyo Chemical Industry Co., Ltd.), which is a silane coupling agent having a chain transfer group, was added to a mixed solution of 50 mL of an aqueous acetic acid solution of pH 3.0 and 50 mL of ethanol. After hydrolyzing the silane coupling agent by stirring the mixture at room temperature for 1 hour, 5 g of silica beads (an average particle diameter of 5 μm, a pore diameter of 70 Å, SMB 70-5 manufactured by Fuji Silysia Chemical Ltd.), which are inorganic particles as an example of an insoluble support, were input thereto and stirred at 70° C. for 2 hours. Thereafter, the silica beads were recovered from the reaction solution by suction filtration and heated at 100° C. for 1 hour. Thereafter, after dispersing in ethanol and shaking well, the supernatant was removed by centrifugal separation and dried.

Synthesis of Polymer

2-Methacryloyloxyethyl phosphorylcholine (hereinafter, will be described as the "MPC monomer," manufactured by Nippon Oil and Fats Co., Ltd.), which is a structural unit of a polymer, was dissolved in ethanol, and thereby 20 mL of a 0.8 mol/L monomer solution was produced. AIBN was added thereto to make 0.027 mol/L, and the mixture was stirred until it became homogeneous. Thereafter, 4 g of the above-described silica beads treated with methacryloxypropyldimethylmethoxysilane were input thereto, and reacted at 70° C. for 6 hours under an argon gas atmosphere. Next, after the silica beads were recovered from the reaction solution by centrifugal separation, dispersed in ethanol, and shaken well, the silica beads were recovered by suction filtration and dried, and thereby a carrier (hereinafter will be simply referred to as the "carrier") in which a polymer containing a structural unit derived from 2-methacryloyloxyethyl phosphorylcholine is immobilized on the silica beads was obtained.

(Measurement of Weight of Polymer-Containing Layer Introduced into Surface of Carrier)

Regarding a weight of a polymer-containing layer introduced to the surface of the carrier obtained above, using a TGA apparatus (TG/DTA6200 manufactured by Seiko Instruments Inc.), a temperature was raised from room temperature to 500° C. at 10° C./min in an air atmosphere, 500° C. was maintained for 1 hour, and then a weight loss ratio was measured. When a weight of the polymer-containing layer introduced to the surface of particles was calculated from the above value, and a surface area of the particles per unit weight separately calculated by a BET method, the weight was 1.08 mg/m$^2$.

Example 1. Check of Physical Properties (Carrier)

In the present example, physical properties of the carrier produced in the above <Synthesis example> were checked from the viewpoint of solid-liquid separation physical properties.

After adding 200 μL of a mixed solution of ethanol:butanol (a volume ratio 1:5, which was used as a solution A) to 10 mg of the carrier produced in the above <Synthesis example> and vigorously dispersing by a vortex, centrifugation was performed with a table-top centrifuge (TOMY, PMC-060), and a degree of separation of a solid-liquid surface of the carrier was checked. It was confirmed that the carrier was settled by centrifugation for 2 to 3 seconds, and the solid-liquid surface became clear. It was confirmed that the solid-liquid surface was clear because the carrier was white (Table 1).

Comparative Example 1. Check of Physical Properties (Sepharose Beads)

In the present comparative example, physical properties of Sepharose beads were checked from the viewpoint of solid-liquid separation physical properties, and were compared with the physical properties of the carrier produced in the above <Synthesis example> by comparison with Example 1.

After adding 200 μL of the solution A of Example 1 to 100 μL of Sepharose beads (SIGMA, Sepharose CL-4B) and vigorously dispersing by a vortex, centrifugation was performed with a table-top centrifuge (TOMY, PMC-060), and a degree of separation of a solid-liquid surface of the Sepharose beads was checked. It was confirmed that the Sepharose beads had not yet settled by centrifugation for 2 to 3 seconds. By continuing the centrifugation for 10 seconds or more, the Sepharose beads were settled, but it was confirmed that the solid-liquid interface was very unclear because a color was translucent (Table 1).

TABLE 1

| | Carrier (Example 1) | Sepharose bead (Comparative Example 2) |
|---|---|---|
| Color | White | Translucent |
| Solid-liquid separation time | A few seconds with table-top centrifuge | 10 seconds or longer with table-top centrifuge |
| Condition of solid-liquid surface | Very clear | Unclear |

Based on the results of Example 1 and Comparative Example 1, it was confirmed that the carrier produced in the above <Synthesis example> has excellent physical properties in solid-liquid separation physical properties, and that solid-liquid separation can be performed easily, simply, and reliably.

Example 2. Concentration of Glycopeptide Using Carrier

In the present example, concentration of glycopeptides from the sample was checked by both batch method and spin column using the carrier produced in the above <Synthesis example>.

(1) Peptide Fragmentation of Protein

50 µL of ultrapure water, 5 µL of 1 M aqueous ammonium bicarbonate solution, and 5 µL of 120 mM dithiothreitol solution were added to 5 mg RNase B (SIGMA), and reacted at 60° C. for 30 minutes. Thereafter, 10 µL of a 123 mM aqueous solution of iodoacetamide was added thereto, and a reaction was carried out under light shielding for 1 hour at room temperature. 400 units of trypsin was added thereto, and the mixture was allowed to react overnight. An appropriate amount of ultrapure water was added thereto to prepare a protein concentration of 50 µg/µL.

(2) Recovery of Glycopeptide

A. Case of Batch Type 1 mg of the beads were added to a 1.5 mL sample tube. After adding 200 µL of the solution A of Example 1 to disperse the beads, centrifugation was performed for a few seconds using a table-top centrifuge. After removing the solution, a sample solution (a mixed solution of 1 µL of the solution prepared in (1) above, 99 µL of ultrapure water, and 600 µL of the solution A of Example 1) was added to a tube containing the carrier produced in the above <Synthesis example>, and stirred vigorously. Thereafter, centrifugation was performed using a table-top centrifuge, the carrier was precipitated, and the solution was removed. Subsequently, 700 µL of ethanol:butanol:water (a volume ratio of 1:5:1, which was used as a washing solution) was added thereto, the mixture was vigorously stirred, and then the carrier was precipitated by centrifugation, and the solution was removed. Furthermore, 700 µL of a 50% aqueous ethanol solution was added thereto, the mixture was vigorously stirred, and then the carrier was precipitated by centrifugation, and the solution was recovered. The recovered solution was dried using a centrifugal evaporator and redissolved in 13 µL of ultrapure water.

B. Case of Spin Column 1 mg of the carrier produced in the above <Synthesis example> was added to a spin column (Ultrafree-MC, Millipore Cat #: UFC30 HVNB). After adding 200 µL of the solution A of Example 1, centrifugation was performed using a table-top centrifuge for a few seconds, and the solution was removed. The sample solution (the mixed solution of 1 µL of the solution prepared in (1) above, 99 µL of ultrapure water, and 600 µL of the solution A of Example 1) was added to the spin column containing the carrier, centrifugation was performed using a table-top centrifuge, and thereby the solution was removed. Subsequently, 700 µL of a washing solution was added, and the solution was removed by centrifugation. Furthermore, 700 µL of a 50% aqueous ethanol solution was added, and the solution was recovered by centrifugation. The recovered solution was dried using a centrifugal evaporator and redissolved in 13 µL of ultrapure water.

(3) LC-MS Analysis

Figure 3:
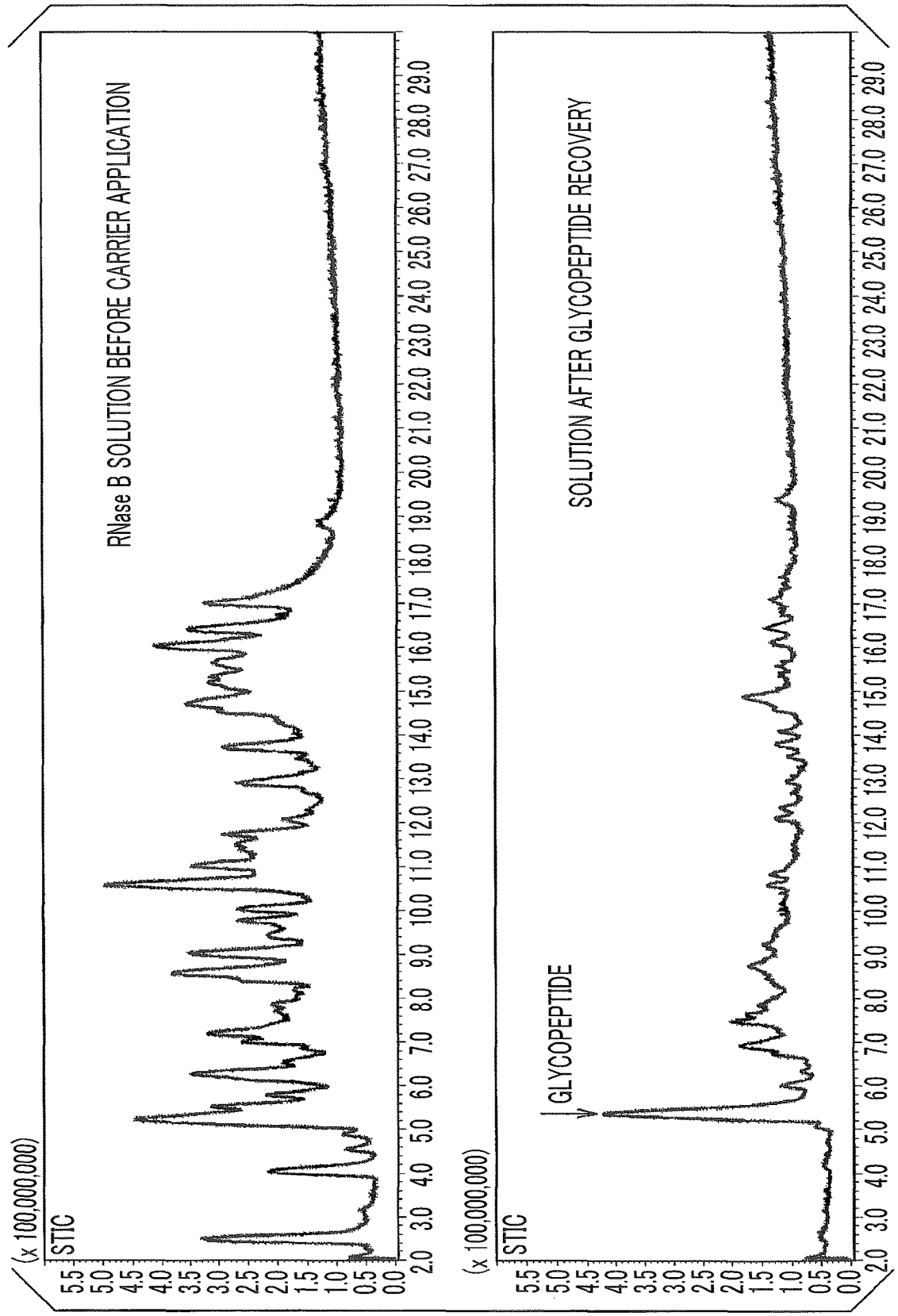
FIG. 3 is a chromatogram showing results of Example 2 in which concentration of glycopeptides using the carrier according to the present embodiment is examined.
Figure 4:
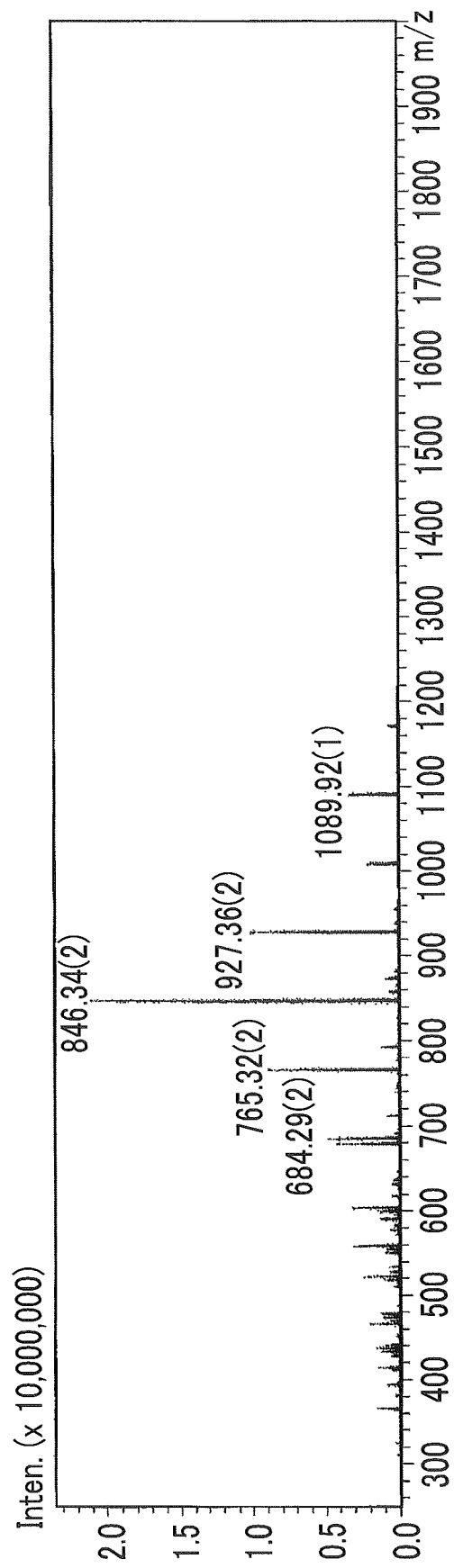
FIG. 4 is a mass spectrum (MS) chart showing results of Example 2 in which concentration of glycopeptides using the carrier according to the present embodiment is examined.

Using 3 µL of each solution prepared in (2) above, LC-MS analysis was performed using the conditions of Table 2. The obtained total ion chromatogram is shown in FIG. 3. In FIG. 3, a horizontal axis represents a retention time (minutes), and a vertical axis represents signal intensity (relative value). It was confirmed that a large number of signals were present in the sample before glycopeptide recovery processing (an upper drawing in FIG. 3). On the other hand, in the sample solution from which the glycopeptide was recovered by the method of the present invention, it was confirmed that a signal was significantly reduced, and a main signal was one (a lower drawing in FIG. 3). The MS results of this main peak (an elution time: 5.2 to 5.8 minutes) are shown in FIG. 4. In FIG. 4, a horizontal axis represents m/z values, and a vertical axis represents signal intensity (relative value). A large number of equally spaced peaks corresponding to one hexose were detected, and it was confirmed that a peak was derived from a peptide to which high mannose, which is a typical sugar chain of RNase B, was bonded. It was confirmed that glycopeptides can be easily concentrated by using the method of the present invention.

TABLE 2

| <LC-MS analysis> | |
| --- | --- |
| LC apparatus: | Nexera (SHIMADZU CORPORATION) |
| LC analysis condition | |
| Column: | TSKgel Super-ODS 2.3 µm (2.0 mm I.D. × 100 mm L.) |
| Column temperature: | 40° C. |
| Mobile phase A: | Aqueous solution of 0.05% formic acid |
| Mobile phase B: | Aqueous solution of 95% acetonitrile containing 0.05% formic acid |
| concentration gradient: | 100% mobile phase A (0 minutes) → 50% mobile phase B (30 minutes) |
| Flow rate: | 0.2 mL/min |
| Injection amount: | 2 µL |
| Detector: | SPD-20A xs (UV 215 nm) |
| Mass spectrometer: | LCMS-IT-TOF (SHIMADZU CORPORATION) |
| Mass spectrometry condition | |
| Ionization mode: | ESI positive ion mode |

Example 3. Concentration of Sugar Chain Using Carrier

In the present example, using the carrier produced in the above <Synthesis example>, concentration of sugar chains from a sample was confirmed using a spin column.

(1) Preparation of Sugar Chain Solution

Oligomers (manufactured by Seikagaku Corporation, product number: 800111) of glucose prepared from hydrolyzate of dextran were dissolved in ultrapure water so that they became 1 mg/mL, and they were used as a sugar chain solution.

(2) Recovery of Sugar Chains 10 mg of the carrier produced in the above <Synthesis example> was added to a spin column (Ultrafree-MC, Millipore Cat #: UFC30 HVNB). After adding 200 µL of ultrapure water, centrifugation was performed using a table-top centrifuge for a few seconds, and the solution was removed. After 990 µL of acetonitrile was added to 10 µL of the solution prepared in the above (1) and mixed well, the mixture was added to a spin column containing the carrier, and centrifuged using a table-top centrifuge to remove the solution. Subsequently, 600 µL of acetonitrile was added, and the solution was removed by centrifugation. Again, 600 µL of acetonitrile was added, and the solution was removed by centrifugation. After adding 100 µL of ultrapure water, and the solution was recovered by centrifugation. The recovered solution was dried using a centrifugal evaporator.

(3) Labeling of Recovered Sugar Chains

10 µL of a 2AB labeling solution (a solution dissolved in a solvent of 30% acetic acid/70% dimethyl sulfoxide so that it became 0.35 M 2-aminobenzamide and 1 M sodium cyanoborohydride) was added to the dry substance obtained in (2) above. After reacting at 60° C. for 2 hours, 90 µL of ultrapure water was added thereto.

(4) HPLC Analysis

Figure 5:
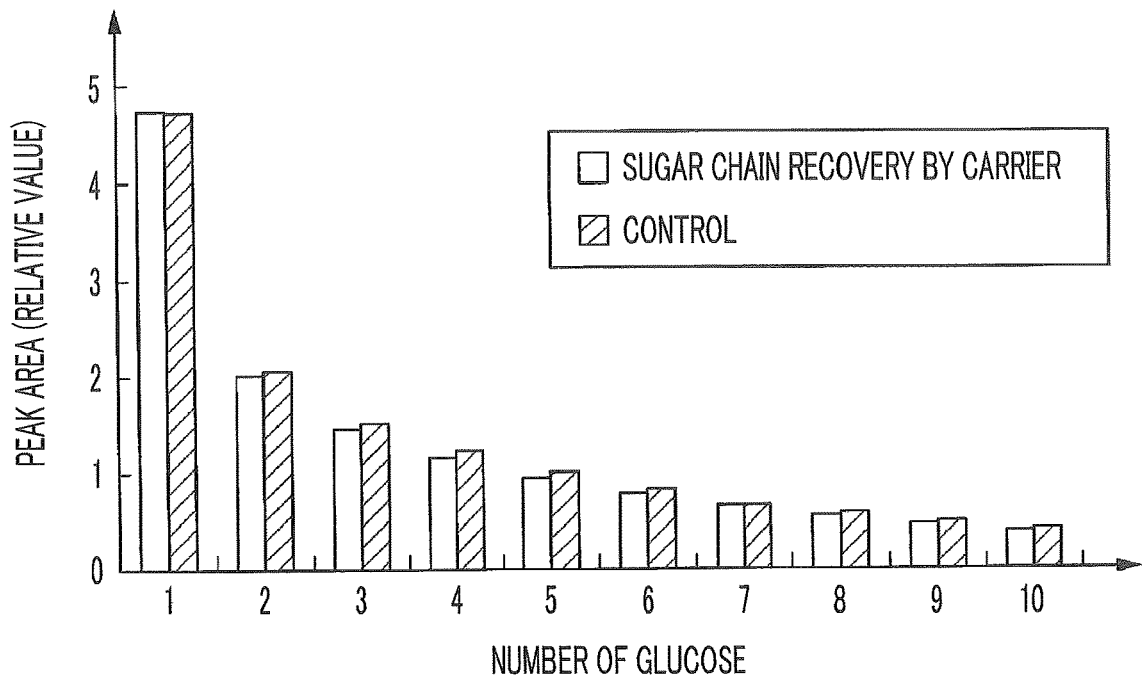
FIG. 5 is a graph showing results of Example 3 in which concentration of sugar chains using the carrier according to the present embodiment is examined, in which a vertical axis represents a peak surface area and a horizontal axis represents the number of glucose.

Using 1 µL of each solution prepared in (3) above, HPLC analysis was performed using the conditions of Table 2. Among the obtained peaks, values of peak areas corresponding to glucose one sugar to ten sugars were checked. The obtained results are shown in FIG. 5. A control sample refers to a sample on which only the process (3) was performed after drying 10 µL of a glucose oligomer solution. The results between the sample subjected to sugar chain recovery with the carrier and the control sample were almost the same, and it was checked that almost no loss of sugar chain occurs when sugar chains are recovered using the carrier.

Comparative Example 2. Concentration of Sugar Chain Using Clean-Up Column

In the present comparative example, sugar chains were concentrated using a known clean-up column of the related art (a column containing a silica-based carrier), and comparison was performed with concentration of sugar chains using the carrier produced in the above <Synthesis example> of Example 3.

(1) Preparation of Sugar Chain Solution

Preparation was performed by the same procedure as in Example 3.

(2) Recovery of Sugar Chains

After adding 200 µL of ultrapure water to a clean-up column (Sumitomo Bakelite, BS-45403 attached product), centrifugation was performed for a few seconds using a table-top centrifuge to remove the solution. After 990 µL of acetonitrile was added to 10 µL of the solution prepared in Preparation of sugar chain solution ((1) above) and mixed well, the mixture was added to a clean-up column containing the carrier, and centrifuged using a table-top centrifuge to remove the solution. Subsequently, 600 µL of acetonitrile was added, and the solution was removed by centrifugation. Again, 600 µL of acetonitrile was added, and the solution was removed by centrifugation. After adding 100 µL of ultrapure water, and the solution was recovered by centrifugation. The recovered solution was dried using a centrifugal evaporator.

(3) Labeling of Recovered Sugar Chains

Preparation was performed by the same procedure as in Example 3.

(4) HPLC Analysis

Figure 6:
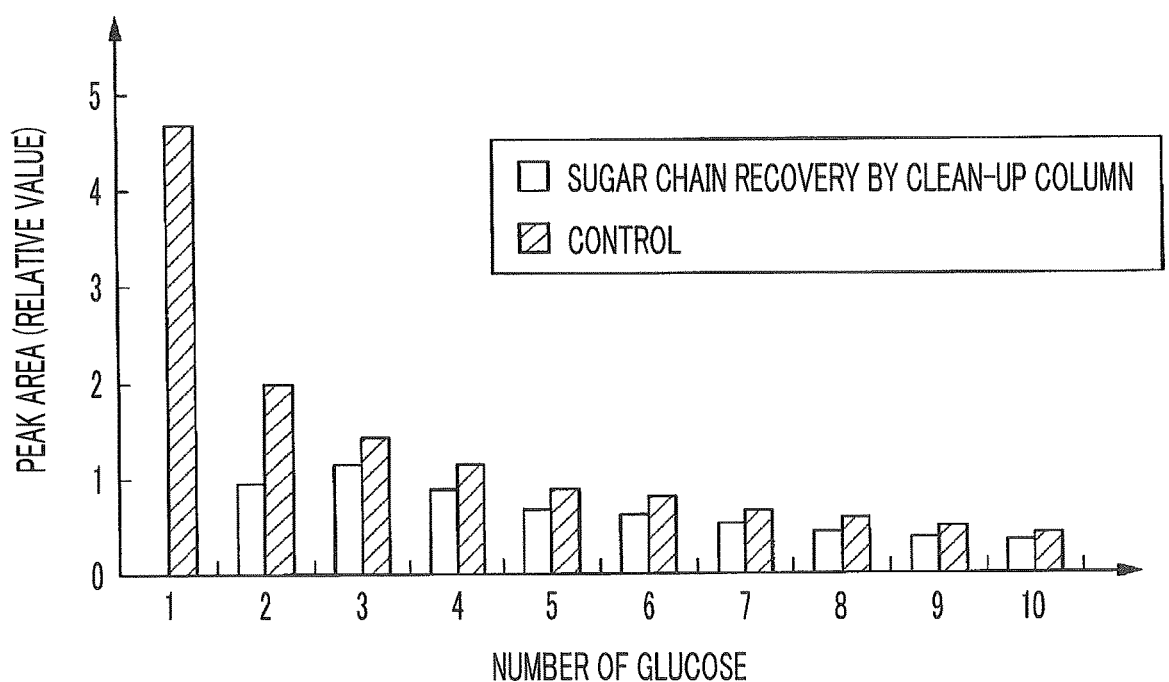
FIG. 6 is a graph showing results of Comparative Example 2 in which concentration of sugar chains using a clean-up column is examined, in which a vertical axis represents a peak surface area and a horizontal axis represents the number of glucose.

Analysis was performed by the same procedure as in Example 3, and among the obtained peaks, values of peak areas corresponding to glucose one sugar to ten sugars were checked. The obtained results are shown in FIG. 6. A control sample refers to a sample on which only the process (3) was performed after drying 10 µL of a glucose oligomer solution. Data showing that the loss of monosaccharides and disaccharides was large was obtained from the samples for which the sugar chain recovery was carried out by the clean-up column. It was checked that a known clean-up column of the related art was insufficient for recovery of small sugar chains such as O-type sugar chains.

Comparative Example 3. Concentration of Sugar Chains Using Graphite Carbon

In the present comparative example, sugar chains were concentrated using a known graphite carbon of the related art, and comparison was performed with concentration of sugar chains using the carrier produced in the above <Synthesis example> of Example 3.

(1) Preparation of Sugar Chain Solution

Preparation was performed by the same procedure as in Example 3.

(2) Recovery of Sugar Chains 1 mL of acetonitrile was allowed to pass through in a graphite carbon column (Sigma Aldrich, Supelclean ENVI-Carb C). Furthermore, 3 mL of water was allowed to pass through. Subsequently, 10 µL of the solution prepared in Preparation of sugar chain solution ((1) above) and 90 µL of 0.1% acetic acid water were mixed and allowed to pass through in the graphite carbon column. 3 mL of water was allowed to pass through to wash the graphitic carbon. After mounting a 0.22 µm filter, 100 µL of ultrapure water was allowed to pass through to recover the solution. The recovered solution was dried using a centrifugal evaporator.

(3) Labeling of Recovered Sugar Chains

Preparation was performed by the same procedure as in Example 3.

(4) HPLC Analysis

Figure 7:
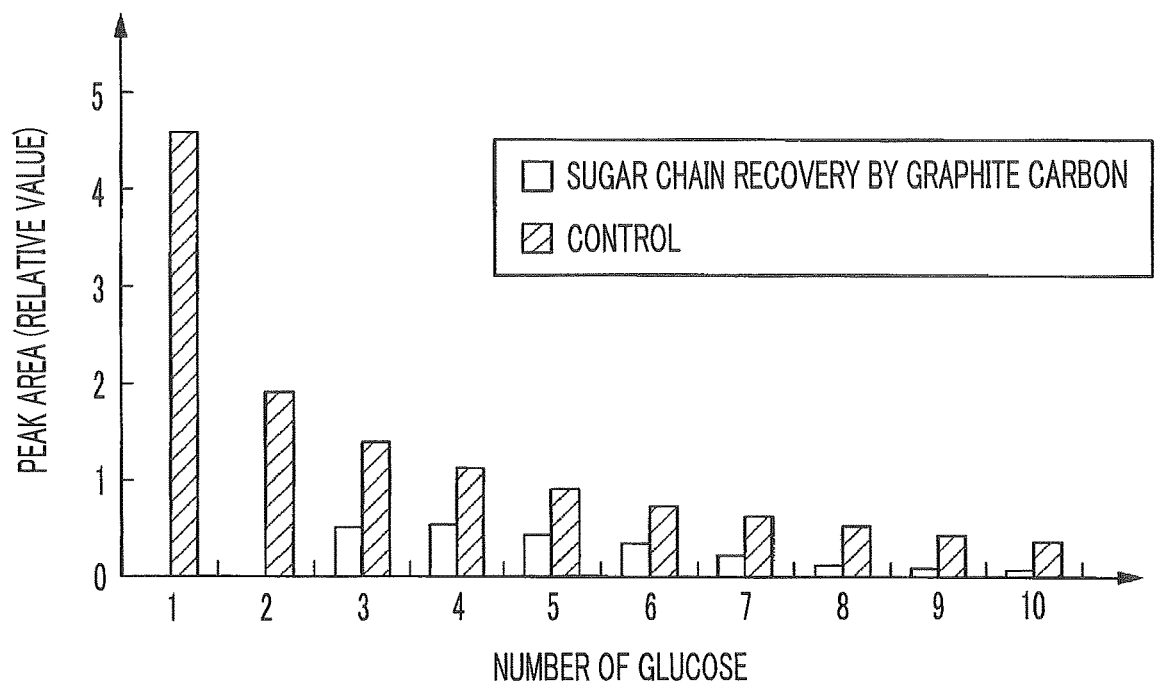
FIG. 7 is a graph showing results of Comparative Example 3 in which concentration of sugar chains using graphite carbon is examined, in which a vertical axis represents a peak surface area and a horizontal axis represents the number of glucose.

Analysis was performed by the same procedure as in Example 3, and among the obtained peaks, values of peak areas corresponding to glucose one sugar to ten sugars were checked. The obtained results are shown in FIG. 7. A control sample refers to a sample on which only the process (3) was performed after drying 10 µL of a glucose oligomer solution. In the sample for which the sugar chain recovery was carried out with the graphite carbon column, loss of sugar occurred overall, and from the sample, data showing that no sugar can be recovered particularly from monosaccharides and disaccharides was obtained. It was checked that a known graphite carbon of the related art is particularly unsuitable for recovery of small sugar chains (monosaccharides, disaccharides, and the like).

By comparison of the results of Example 3 and the results of Comparative Examples 2 and 3, the carrier produced in the above <Synthesis example> hardly causes loss when recovering sugar chains, and therefore it can be understood that the carrier can be suitably used for recovery of small sugar chains (monosaccharides, disaccharides, and the like), which was difficult in the related art.

Example 4. Concentration of Sugar Chains Using Purification Agent

In the present example, using a purification agent in which a betaine structure represented by Formula (2) was introduced into a crosslinked polystyrene skeleton, concentration of sugar chains from a sample was checked using a spin column.

(2)

(1) Preparation of Sugar Chain Solution

Preparation was performed by the same procedure as in Example 3.

(2) Recovery of Sugar Chains 10 mg of the above-mentioned purification agent was added to a spin column (Ultrafree-MC, Millipore Cat #: UFC30HVNB). After adding 200 μL of acetonitrile, centrifugation was performed using a table-top centrifuge for a few seconds, and the solution was removed. After 990 μL of acetonitrile was added to 10 μL of the solution prepared in the above (1) and mixed well, the mixture was added to a spin column containing the purification agent, and centrifuged using a table-top centrifuge to remove the solution. Subsequently, 600 μL of acetonitrile was added, and the solution was removed by centrifugation. Again, 600 μL of acetonitrile was added, and the solution was removed by centrifugation. After adding 100 μL of ultrapure water, and the solution was recovered by centrifugation. The recovered solution was dried using a centrifugal evaporator.

(3) Labeling of Recovered Sugar Chains

Preparation was performed by the same procedure as in Example 3.

(4) HPLC Analysis

Figure 8:
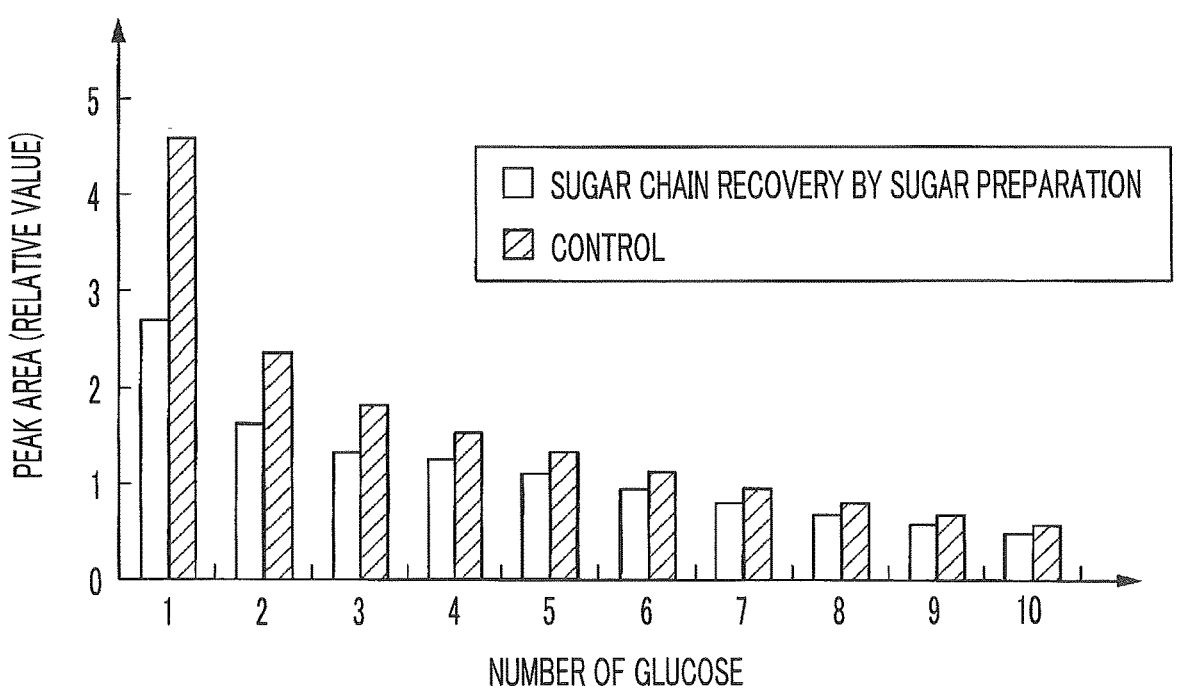
FIG. 8 is a graph showing results of Example 4 in which concentration of sugar chains using the carrier according to the present embodiment is examined, in which a vertical axis represents a peak surface area and a horizontal axis represents the number of glucose.

Analysis was performed by the same procedure as in Example 3, and among the obtained peaks, values of peak areas corresponding to glucose one sugar to ten sugars were checked. The obtained results are shown in FIG. 8. A control sample refers to a sample on which only the process (3) was performed after drying 10 μL of a glucose oligomer solution. It was checked that, although the sample subjected to sugar chain recovery with the purification agent had some loss compared to the control sample, it was also possible to recover small sugars such as monosaccharides and disaccharides.

INDUSTRIAL APPLICABILITY

According to the present invention, the present invention can provide a technique capable of specifically and efficiently capturing hydrophilic glycopeptides and sugar chains. Accordingly, the present invention can be utilized in technical fields requiring concentration of glycopeptides and sugar chains, for example, in technical fields of life science, medicine, and drug discovery, such as mechanism of onset of various diseases accompanied by sugar chain structural change, and development of disease treatment and diagnosis technology.

REFERENCE SIGNS LIST

100: apparatus for preparing sugar chains of glycoproteins, 10: carrier, 15: container, 16: recovery container, 20: container holding part, 30: reagent introduction part, 31: sample, 32: washing solution, 33: eluate, 34: tank, 35: sample introduction part (washing solution introduction part, eluate introduction part) 35a: liquid sending pipe, 36, 37, 38: valve, 40: solid-liquid separation part, 41: rack, 42: drive shaft, 43: motor, 50: container transfer part (liquid transfer part), 60: temperature regulation part

The invention claimed is:

1. A method for purifying an O-glycosidic bonded sugar chain, the method comprising:
bringing a purification agent into contact with a sample containing an O-glycosidic bonded sugar chain and containing an organic solvent such that the sugar chain is adsorbed onto the purification agent;
subjecting the purification agent having the O-glycosidic bonded sugar chain adsorbed thereon to solid-liquid separation, so as to remove a liquid phase portion from the purification agent; and
bringing the purification agent into contact with water to elute the O-glycosidic bonded sugar chain,
wherein:
the purification agent comprises a compound having a betaine structure;
the betaine structure comprises a cationic group and an anionic group;
the cationic group is a quaternary ammonium group; and
the anionic group is a phosphoric acid group.

2. The method according to claim 1,
wherein the betaine structure further comprises a linker which links the cationic group and the anionic group, and
wherein the linker is an alkylene group having 1 to 10 carbon atoms.

3. The method according to claim 1, wherein the betaine structure is a phosphorylcholine group.

4. The method according to claim 1, wherein the compound is a polymer in which a side chain having a betaine structure is bonded to a main chain.

5. The method according to claim 4, wherein the polymer is a polymer of a monomer containing a (meth)acrylic compound.

6. The method according to claim 1, wherein the purification agent is immobilized on an insoluble support.

7. The method according to claim 4, wherein the purification agent is immobilized on an insoluble support.

8. The method according to claim 7, wherein a weight of the polymer immobilized on the insoluble support is 0.5 mg to 1.5 mg per unit surface area ($m^2$) of the insoluble support.

9. The method according to claim 6, wherein the insoluble support is formed of an inorganic substance.

10. The method according to claim 6, wherein a specific gravity of the purification agent is 1.05 to 3.00.

11. The method according to claim 6, which is a spherical shape and has an average particle diameter of 0.5 μm to 100 μm.

12. The method according to claim 1, further comprising:
washing the purification agent having the O-glycosidic bonded sugar chain adsorbed thereon with the organic solvent.

* * * * *